(12) United States Patent
Mortlock et al.

(10) Patent No.: US 6,977,259 B2
(45) Date of Patent: Dec. 20, 2005

(54) QUINOLINE DERIVATIVES AND THEIR USE AS AURORA 2 KINASE INHIBITORS

(75) Inventors: Andrew Austen Mortlock, Macclesfield (GB); Frederic Henri Jung, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/182,454

(22) PCT Filed: Jan. 24, 2001

(86) PCT No.: PCT/GB01/00245

§ 371 (c)(1),
(2), (4) Date: Jul. 26, 2002

(87) PCT Pub. No.: WO01/55116

PCT Pub. Date: Aug. 2, 2001

(65) Prior Publication Data

US 2003/0105129 A1 Jun. 5, 2003

(30) Foreign Application Priority Data

Jan. 28, 2000 (EP) .......................................... 00400228

(51) Int. Cl.$^7$ .................. A61K 31/4965; A61K 31/505; A01N 43/54; C07D 239/02; C07D 401/00
(52) U.S. Cl. ........................... 514/255.05; 514/255.06; 514/275; 544/322; 544/331; 544/405
(58) Field of Search ....................... 514/255.05, 255.06, 514/275, 235.2; 544/322, 331, 405, 122

(56) References Cited

U.S. PATENT DOCUMENTS 3,075,981 A * 1/1963 Surrey ........................ 544/331

FOREIGN PATENT DOCUMENTS

| EP | 0 860 433 A1 | 8/1998 |
|---|---|---|
| FR | 2.154.326 | 5/1973 |
| WO | WO 92/20642 A1 | 11/1992 |
| WO | WO 96/09294 A1 | 3/1996 |
| WO | WO 99/35132 A1 | 7/1999 |
| WO | WO 99/35146 A1 | 7/1999 |
| WO | WO 01/40218 A1 | 6/2001 |

OTHER PUBLICATIONS

Hawley's Condensed Chemical Dictionary, 13$^{th}$ ed., pp. 825 and 837 © 1997 by Van Nostrand Reinhold.*
Ganapathi et al., Chem Abstract 47:22276.*
Abdel–Halim et al., Chem. Abstract 121:35528.*
Ishikawa et al., Chem. Abstract 121: 134158.*

Abdel–Halim, A.M. et al. Synthesis and biological activity of some 4–(p–chlorophenyl)–6–(o–hydroxyphenyl)–2–aminopyrimidine derivatives: Part 1. Chemical Abstracts 121, 1011 (Abstract No. 121: 35528) (Jul. 18, 1994).
Gargallo, J.C. 4–(2–Pyridylamino)–7–chloroquinoline. Chemical Abstracts 61, 14646 (Dec. 1, 1964).
Ishikawa, K. et al. Preparation of 3–[(2–pyrimidinyl and 2–triazinyl)amino] quinoline derivatives as agrochemical fungicides. Chemical Abstracts 121, 1040 (Abstract No. 134158) (Sep. 12, 1994).
Kubo, K. et al. A Novel Series of 4–Phenoxyquinolines: Potent and Highly Selective Inhibitors of PDGF Receptor Autophosphorylation. Bioorganic & Medicinal Chem. Letts. 7, 2935–2940 (1997).

* cited by examiner

Primary Examiner—James O. Wilson
Assistant Examiner—Zachary C. Tucker

(57) ABSTRACT

A compound of formula (I)

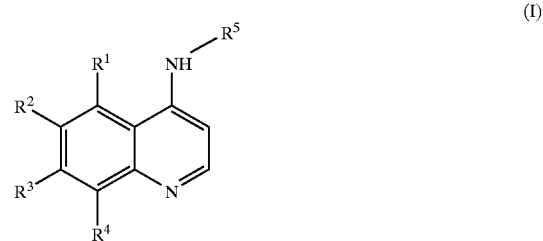

or a salt, ester, amide or prodrug thereof; $R^5$ is an optionally substituted 6-membered aromatic ring containing at least one nitrogen atom, and $R^1$, $R^2$, $R^3$, $R^4$ are independently selected from halogeno, cyano, nitro, $C_{1-3}$alkylsulphonyl, —N(OH)$R^7$— (wherein $R^7$ is hydrogen, or $C_{1-3}$ alkyl), or $R^9X^1$— (wherein $X^1$ represents a direct bond, —O—, —CH$_2$—, —OC(O)—, —C(O)—, —S—, —SO—, —SO$_2$—, —NR$^{10}$C(O)—, —C(O)NR$^{11}$—, —SO$_2$NR$^{12}$—, —NR$^{13}$SO$_2$— or —NR$^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is hydrogen, optionally substituted hydrocarbyl, optionally substituted heterocyclyl or optionally substituted alkoxy); provided that at least one of $R^2$ or $R^3$ is other than hydrogen. These compounds are inhibitors of aurora 2 kinase. Thus they, and pharmaceutical compositions containing them, are useful in methods of treatment of proliferative disease such as cancer and in particular cancers such as colorectal or breast cancer where aurora 2 is upregulated.

12 Claims, No Drawings

QUINOLINE DERIVATIVES AND THEIR USE AS AURORA 2 KINASE INHIBITORS

CROSS-REFERENCE TO RELATED APPLICATIONS

This application is a national stage filing under 35 U.S.C. 371 of PCT application PCT/GB01/00245, filed Jan. 24, 2001, which claims priority to European Application No. 00400228.3, filed Jan. 28, 2000, the specifications of each of which are incorporated by reference herein. PCT Application PCT/GB01/00245 was published under PCT Article 21(2) in English.

The present invention relates to novel quinoline derivatives useful in the treatment of certain diseases in particular to proliferative disease such as cancer, to process for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle For example, the CDK4 protein appears to control entry into the cell cycle (the G0–G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672–1677; Pines, 1995, Seminars in Cancer Biology 6: 63–72). Other studies (Loda et al., 1997, Nature Medicine 3(2): 231–234; Gemma et al., 1996, International Journal of Cancer 68(5): 605–11; Elledge et al. 1996, Trends in Cell Biology 6; 388–392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ipl1 proteins. *Drosophila* aurora and *S. cerevisiae* Ipl1, which are highly homologous at the amino acid sequence level, encode serine/threonine protein kinases. Both aurora and Ipl1 are known to be involved in controlling the transition from the G2 phase of the cell cycle through mitosis, centrosome function, formation of a mitotic spindle and proper chromosome separation/segregation into daughter cells. The two human homologues of these genes, termed aurora1 and aurora2, encode cell cycle regulated protein kinases. These show a peak of expression and kinase activity at the G2/M boundary (aurora2) and in mitosis itself (aurora1). Several observations implicate the involvement of human aurora proteins, and particularly aurora2 in cancer. The aurora2 gene maps to chromosome 20q13, a region that is frequently amplified in human tumours including both breast and colon tumours. Aurora2 may be the major target gene of this amplicon, since aurora2 DNA is amplified and aurora2 mRNA overexpressed in greater than 50% of primary human colorectal cancers. In these tumours aurora2 protein levels appear greatly elevated compared to adjacent normal tissue. In addition, transfection of rodent fibroblasts with human aurora2 leads to transformation, conferring the ability to grow in soft agar and form tumours in nude mice (Bischoff et al., 1998, The EMBO Journal. 17(11): 3052–3065). Other work (Zhou et al., 1998, Nature Genetics. 20(2): 189–93) has shown that artificial overexpression of aurora2 leads to an increase in centrosome number and an increase in aneuploidy.

Importantly, it has also been demonstrated that abrogation of aurora2 expression and function by antisense oligonucleotide treatment of human tumour cell lines (WO 97/22702 and WO 99/37788) leads to cell cycle arrest in the G2/M phase of the cell cycle and exerts an antiproliferative effect in these tumour cell lines. There is considerable evidence that G2/M arrest, resulting (for example) from disruption of assembly of the mitotic spindle by microtubule binding drugs such as paclitaxel leads to the induction of apoptosis in tumour cells in a manner distinct from inhibition of e.g. the EGF receptor, (Kottke et al. 1999 Journal of Biological Chemistry 274 (22) 15927–15936, reviewed in Blagosklonny et ql., 1999, International Journal of Cancer 83: 151–156). This indicates that inhibition of the function of aurora2 will have an antiproliferative effect, and may have an apoptosisinducing effect, that may be useful in the treatment of human tumours and other hyperproliferative diseases Certain heterocyclic derivatives have been proposed hitherto for use in the inhibition of protein tyrosine kinase in WO 99/35132.

The applicants have found a series of compounds which inhibit the effect of the aurora2 kinase and which are thus of use in the treatment of proliferative disease such as cancer, in particular in such diseases such as colorectal or breast cancer where aurora 2 kinase is known to be active.

The present invention provides a compound of formula (I)

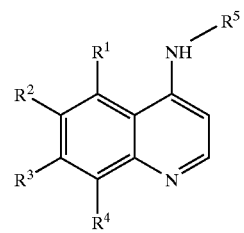

or a salt, ester, amide or prodrug thereof;

where $R^5$ is an optionally substituted 6-membered aromatic ring containing at least one nitrogen atom, and $R^1$, $R^2$, $R^3$, $R^4$ are independently selected from halogeno, cyano, nitro, $C_{1-3}$alkylsulphanyl, —N(OH)$R^7$— (wherein $R^7$ is hydrogen, or $C_{1-3}$alkyl), or $R^9X^1$— (wherein $X^1$ represents a direct bond, —O—, —CH$_2$—, —OC(O)—, —C(O)—, —S—, —SO—, —SO$_2$—, —NR$^{10}$C(O)—, —C(O)NR$^{11}$—, —SO$_2$NR$^{12}$—, —NR$^{13}$SO$_2$— or —NR$^{14}$— (wherein R$^{10}$, R$^{11}$, R$^{12}$, R$^{13}$ and R$^{14}$ each independently represents hydrogen, C$_{1-3}$alkyl, hydroxyC$_{1-4}$alkyl or C$_{1-3}$alkoxyC$_{2-3}$alkyl), and R$^9$ is hydrogen, optionally substituted hydrocarbyl, optionally substituted heterocyclyl or optionally substituted alkoxy; provided that at least one of R$^2$ or R$^3$ is other than hydrogen.

In this specification the term 'alkyl' when used either alone or as a suffix includes straight chained, branched structures. Unless otherwise stated, these groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" includes aromatic or non-aromatic rings, for example containing from 4 to 20, suitably from 5 to 8 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. The moiety may be saturated or unsaturated. For example, these may be alkyl, alkenyl, alkynyl, aryl, aralkyl, cycloalkyl, cycloalkenyl or cycloalkynyl, or combinations thereof.

Examples of such combinations are alkyl, alkenyl or alkynyl substituted with aryl, aralkyl, cycloalkyl, cycloalkenyl or cycloalkynyl, or an aryl, heterocyclyl, alkoxy, aralkyl, cycloalkyl, cycloalkenyl or cycloalkynyl substituted with alkyl, alkenyl, alkynyl or alkoxy, but others may be envisaged.

In particular hydrocarbyl groups include alkyl, alkenyl, alkynyl, aryl, aralkyl, cycloalkyl, cycloalkenyl or cycloalkynyl.

The term "functional group" refers to reactive substituents such as nitro, cyano, halo, oxo, =CR$^{78}$R$^{79}$, C(O)$_x$R$^{77}$, OR$^{77}$, S(O)$_y$R$^{77}$, NR$^{78}$R$^{79}$, C(O)NR$^{78}$R$^{79}$, OC(O)NR$^{78}$R$^{79}$, =NOR$^{77}$, —NR$^{77}$C(O)$_x$R$^{78}$, —NR$^{77}$CONR$^{78}$R$^{79}$, —N=CR$^{78}$R$^{79}$, S(O)$_y$NR$^{78}$R$^{79}$ or —NR$^{77}$S(O)$_y$R$^{78}$ where R$^{77}$, R$^{78}$ and R$^{79}$ are independently selected from hydrogen, optionally substituted hydrocarbyl, optionally substituted hetercyclyl or optionally substituted alkoxy, or R$^{78}$ and R$^{79}$ together form an optionally substituted ring which optionally contains further heteroatoms such as oxygen, nitrogen, S, S(O) or S(O)$_2$, where x is an integer of 1 or 2, y is 0 or an integer of 1–3.

Suitable optional substituents for hydrocarbyl, heterocyclyl or alkoxy groups R$^{77}$, R$^{78}$ and R$^{79}$ as well as rings formed by R$^{78}$ and R$^{79}$ include halo, perhaloalkyl such as trifluoromethyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_y$R$^{90}$ where y is as defined above and R$^{90}$ is a hydrocarbyl group such as alkyl.

In particular, optional substituents for hydrocarbyl, hetercyclyl or alkoxy groups R$^{77}$, R$^{78}$ and R$^{79}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_y$R$^{90}$ where y is as defined above and R$^{90}$ is a hydrocarbyl group such as alkyl.

Certain compounds of formula (I) may include a chiral centre and the invention includes all enantiomeric forms thereof, as well as mixtures thereof including racemic mixtures.

In particular, R$^9$ is hydrogen or an alkyl group, optionally substituted with one or more groups selected from functional groups as defined above, or alkenyl, alkynyl, aryl, heterocyclyl, cycloalkyl, cycloalkenyl or cycloalkynyl, any of which may be substituted with a functional group as defined above, and where any aryl, heterocyclyl, cycloalkyl, cycloalkenyl, cycloalkynyl groups may also be optionally substituted with hydrocarbyl such as alkyl, alkenyl or alkynyl.

For example, R$^9$ is selected from one of the following twenty-two groups:

1) hydrogen or C$_{1-5}$alkyl which may be unsubstituted or which may be substituted with one or more functional groups;
2) —R$^a$X$^2$C(O)R$^{15}$ (wherein X$^2$ represents —O— or —NR$^{16}$— (in which R$^{16}$ represents hydrogen, or alkyl optionally substituted with a functional group) and R$^{15}$ represents C$_{1-3}$alkyl, —NR$^{17}$R$^{18}$ or —OR$^{19}$ (wherein R$^{17}$, R$^{18}$ and R$^{19}$ which may be the same or different each represents hydrogen, or alkyl optionally substituted with a functional group);
3) —R$^b$X$^3$R$^{20}$ (wherein X$^3$ represents —O—, —C(O)—, —S—, —SO—, —SO$_2$—, —OC(O)—, —NR$^{21}$C(O)$_s$—, —C(O)NR$^{22}$—, —SO$_2$NR$^{23}$—, —NR$^{24}$SO$_2$— or —NR$^{25}$— (wherein R$^{21}$, R$^{22}$, R$^{23}$, R$^{24}$ and R$^{25}$ each independently represents hydrogen, or alkyl optionally substituted with a functional group and s is 1 or 2) and R$^{20}$ represents hydrogen, hydrocarbyl (as defined herein) or a saturated heterocyclic group, wherein the hydrocarbyl or heterocyclic groups may be optionally substituted by one or more functional groups and the heterocyclic groups may additionally be substituted by a hydrocarbyl group;
4) —R$^c$X$^4$R$^{c'}$X$^5$R$^{26}$ (wherein X$^4$ and X$^5$ which may be the same or different are each —O—, —C(O)—, —S—, —SO—, —SO$_2$—, —OC(O)—, —NR$^{27}$C(O)$_s$—, —C(O)$_x$NR$^{28}$—, —SO$_2$NR$^{29}$—, —NR$^{30}$SO$_2$— or —NR$^{31}$— (wherein R$^{27}$, R$^{28}$, R$^{29}$, R$^{30}$ and R$^{31}$ each independently represents hydrogen or alkyl optionally substituted by a functional group and s is 1 or 2) and R$^{26}$ represents hydrogen, or alkyl optionally substituted by a functional group;
5) R$^{32}$ wherein R$^{32}$ is a C$_{3-6}$ cycloalkyl or saturated heterocyclic ring (linked via carbon or nitrogen), which cycloalkyl or heterocyclic group may be substituted by one or more functional groups or by a hydrocarbyl or heterocyclyl group which hydrocarbyl or heterocyclyl group may be optionally substituted by one or more functional groups;

6) —$R^dR^{32}$ (wherein $R^{32}$ is as defined hereinbefore);
7) —$R^eR^{32}$ (wherein $R^{32}$ is as defined hereinbefore);
8) —$R^fR^{32}$ (wherein $R^{32}$ is as defined hereinbefore);
9) $R^{33}$ (wherein $R^{33}$ represents a pyridone group, an aryl group or an aromatic heterocyclic group (linked via carbon or nitrogen) with 1–3 heteroatoms selected from O, N and S, which pyridone, aryl or aromatic heterocyclic group may be substituted by one or more functional groups or by a hydrocarbyl group optionally substituted by one or more functional groups or heterocyclyl groups, or by a heterocyclyl group optionally susbsituted by one or more functional groups or hydrocarbyl groups;
10) —$R^gR^{33}$ (wherein $R^{33}$ is as defined hereinbefore);
11) —$R^hR^{33}$ (wherein $R^{33}$ is as defined hereinbefore);
12) —$R^iR^{33}$ (wherein $R^{33}$ is as defined hereinbefore);
13) —$R^jX^6R^{33}$ (wherein $X^6$ represents —O—, —S—, —SO—, —SO$_2$—, —OC(O)—, —NR$^{38}$C(O)—, —C(O)NR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, or alkyl optionally substituted with a functional group) and $R^{37}$ is as defined hereinbefore);
14) —$R^kX^7R^{33}$ (wherein $X^7$ represents —O—, —C(O)—, —S—, —SO—, —SO$_2$—, —OC(O)—, —NR$^{43}$C(O)—, —C(O)NR$^{44}$—, —SO$_2$NR$^{45}$—, —NR$^{46}$SO$_2$— or —NR$^{47}$— (wherein $R^{43}$, $R^{44}$, $R^{45}$, $R^{46}$ and $R^{47}$ each independently represents hydrogen, or alkyl optionally substituted with a functional group) and $R^{33}$ is as defined hereinbefore);
15) —$R^mX^8R^{33}$ (wherein $X^8$ represents —O—, —C(O)—, —S—, —SO—, —SO$_2$—, —OC(O)—, —NR$^{48}$C(O)—, —C(O)NR$^{49}$—, —SO$_2$NR$^{50}$—, —NR$^{51}$SO$_2$— or —NR$^{52}$— (wherein $R^{48}$, $R^{49}$, $R^{50}$, $R^{51}$ and $R^{52}$ each independently represents hydrogen, hydrogen, or alkyl optionally substituted with a functional group) and $R^{33}$ is as defined hereinbefore);
16) —$R^nX^9R^{n'}R^{33}$ (wherein $X^9$ represents —O—, —C(O)—, —S—, —SO—, —SO$_2$—, —OC(O)—, —NR$^{53}$C(O)—, —C(O)NR$^{54}$—, —SO$_2$NR$^{55}$—, —NR$^{56}$SO$_2$— or —NR$^{57}$— (wherein $R^{53}$, $R^{54}$, $R^{55}$, $R^{56}$ and $R^{57}$ each independently represents hydrogen, hydrogen, or alkyl optionally substituted with a functional group) and $R^{33}$ is as defined hereinbefore);
17) —$R^pX^9$—$R^{p'}R^{32}$ (wherein $X^9$ and $R^{32}$ are as defined hereinbefore);
18) $C_{2-5}$alkenyl which may be unsubstituted or which may be substituted with one or more functional groups;
19) $C_{2-5}$alkynyl which may be unsubstituted or which may be substituted with one or more functional groups;
20) —$R^tX^9R^tR^{32}$ (wherein $X^9$ and $R^{32}$ are as defined hereinbefore);
21) —$R^uX^9R^uR^{32}$ (wherein $X^9$ and $R^{32}$ are as defined hereinbefore); and
22) —$R^vR^{58}(R^{v'})_q(X^9)_rR^{59}$ (wherein $X^9$ is as defined hereinbefore, q is 0 or 1, r is 0 or 1, and $R^{58}$ is a $C_{1-3}$alkylene group or a cyclic group selected from divalent cycloalkyl or heterocyclic group, which $C_{1-3}$alkylene group may be substituted by one or more functional groups and which cyclic group may be substituted by one or more functional groups or by a hydrocarbyl group optionally substituted by one or more functional groups or heterocyclyl groups, or by a heterocyclyl group optionally substituted by one or more functional groups or hydrocarbyl groups; and $R^{59}$ is hydrogen, $C_{1-3}$alkyl, or a cyclic group selected from cycloalkyl or heterocyclic group, which $C_{1-3}$alkylene group may be substituted by one or more functional groups and which cyclic group may be substituted by one or more may be substituted by one or more functional groups or by a hydrocarbyl group optionally substituted by one or more functional groups or heterocyclyl groups, or by a heterocyclyl group optionally substituted by one or more functional groups or hydrocarbyl groups;

and wherein $R^a$, $R^b$, $R^{b'}$, $R^c$, $R^{c'}$, $R^d$, $R^g$, $R^j$, $R^n$, $R^{n'}$, $R^p$, $R^{p'}$, $R^t$, $R^u$, $R^v$ and $R^{v'}$ are independently selected from $C_{1-8}$alkylene groups optionally substituted by one or more substituents functional groups, $R^eR^h$, $R^k$ and $R^t$ are independently selected from $C_{2-8}$alkenylene groups optionally substituted by one or more functional groups, and $R^f$, $R^i$, $R^m$ and $R^u$ are independently selected from by $C_{2-8}$alkynylene groups optionally substituted by one or more functional groups.

For example, $R^9$ is selected from one of the following twenty-two groups:

1) hydrogen or $C_{1-5}$alkyl which may be unsubstituted or which may be substituted with one or more groups selected from hydroxy, oxiranyl, fluoro, chloro, bromo and amino (including $C_{1-3}$alkyl and trifluoromethyl);
2) —$R^aX^2C(O)R^{15}$ (wherein $X^2$ represents —O— or —NR$^{16}$— (in which $R^{16}$ represents hydrogen, $C_{1-3}$alkyl or $C_{1-3}$alkoxyC$_{2-3}$alkyl) and $R^{15}$ represents $C_{1-3}$alkyl, —NR$^{17}$R$^{18}$ or —OR$^{19}$ (wherein $R^{17}$, $R^{18}$ and $R^{19}$ which may be the same or different each represents hydrogen, $C_{1-5}$alkyl. hydroxyC$_{1-5}$alkylor $C_{1-3}$alkoxyC$_{2-3}$alkyl));
3) —$R^bX^3R^{20}$ (wherein $X^3$ represents —O—, C(O)—S—, —SO—, —SO$_2$—, —OC(O)—, —NR$^{21}$C(O)$_s$—, —C(O)NR$^{22}$—, —SO$_2$NR$^{23}$, —NR$^{24}$SO$_2$— or —NR$^{25}$— (wherein $R^{21}$, $R^{22}$, $R^{23}$, $R^{24}$ and $R^{25}$ each independently represents hydrogen, $C_{1-3}$alkyl, hydroxy $C_{1-4}$alkyl or $C_{1-3}$alkoxyC$_{2-3}$alkyl and s is 1 or 2) and $R^{20}$ represents hydrogen, $C_{1-6}$alkyl, $C_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which $C_{1-6}$alkyl group may bear 1, 2 or 3 substituents selected from oxo, hydroxy, halogeno, cyclopropyl, amino, $C_{1-4}$alkylamino, $C_{1-4}$alkanoyldi-$C_{1-4}$alkylamino, $C_{1-4}$alkylthio, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxyC$_{1-4}$alkyl, $C_{1-4}$alkylsulphonylC$_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylaminoC$_{1-4}$alkyl, di($C_{1-4}$alkyl)aminoC$_{1-4}$alkyl, $C_{1-4}$alkylaminoC$_{1-4}$alkoxy, di($C_{1-4}$alkyl)aminoC$_{1-4}$alkoxy and a group —(—O—)$_f$(R$^b$)$_g$D (wherein f is 0 or 1, g is 0 or 1 and D is a cyclic group selected from $C_{3-6}$cycloalkyl group, an aryl group or a 5–6-membered saturated heterocyclic group with 1–2 heteroatoms, selected independently from O, S and N, which cyclic group may bear one or more substituents selected from halo or $C_{1-4}$alkyl));
4) —$R^cX^4R^cX^5R^{26}$ (wherein $X^4$ and $X^5$ which may be the same or different are each —O—, C(O), —S—, —SO—, —SO$_2$—, —NR$^{27}$C(O)$_s$—, —C(O)$_x$NR$^{28}$—, —SO$_2$NR$^{29}$—, —NR$^{30}$SO$_2$— or —NR$^{31}$— (wherein $R^{27}$, $R^{28}$, $R^{29}$, $R^{30}$ and $R^{31}$ each independently represents hydrogen, $C_{1-3}$alkyl or $C_{1-3}$alkoxyC$_{2-3}$alkyl and s is 1 or 2) and $R^{26}$ represents hydrogen, $C_{1-3}$alkyl,hydroxyC$_{1-3}$alkylorC$_{1-3}$alkoxyC$_{2-3}$alkyl);

5) $R^{32}$ (wherein $R^{32}$ is a 4–6-membered cycloalkyl or saturated heterocyclic ring (linked via carbon or nitrogen) with 1–2 heteroatoms, selected independently from O, S and N, which cycloalkyl or heterocyclic group may bear 1 or 2 substituents selected from oxo, hydroxy, halogeno, cyano, $C_{1-4}$alkyl, hydroxy$C_{1-4}$alkyl, cyano$C_{1-4}$alkyl, cyclopropyl, $C_{1-4}$alkylsulphonyl$C_{1-4}$alkyl, $C_{1-4}$alkoxycarbonyl, carboxamido, $C_{1-4}$aminoalkyl, $C_{1-4}$alkylamino, di($C_{1-4}$alkyl)amino, $C_{1-4}$alkylamino$C_{1-4}$ alkyl, $C_{1-4}$alkanoyl, di($C_{1-4}$alkyl)amino$C_{1-4}$alkyl, $C_{1-4}$alkylamino$C_{1-4}$alkoxy, di($C_{1-4}$alkyl)amino$C_{1-4}$ alkoxy nitro, amino, $C_{1-4}$alkoxy, $C_{1-4}$hydroxyalkoxy, carboxy, trifluoromethyl, —C(O)NR$^{38}$R$^{39}$, —NR$^{40}$C(O) R$^{41}$ (wherein R$^{38}$, R$^{39}$, R$^{40}$ and R$^{41}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);
6) —R$^d$R$^{32}$ (wherein R$^{32}$ is as defined hereinbefore);
7) —R$^e$R$^{32}$ (wherein R$^{32}$ is as defined hereinbefore);
8) —R$^f$R$^{32}$ (wherein R$^{32}$ is as defined hereinbefore);
9) R$^{33}$ (wherein R$^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, nitro, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, oxo, cyano$C_{1-4}$ alkyl, cyclopropyl, $C_{1-4}$alkylsulphonyl$C_{1-4}$alkyl, $C_{1-4}$alkoxycarbonyl, di($C_{1-4}$alkyl)amino, $C_{1-4}$alkylamino$C_{1-4}$alkyl, $C_{1-4}$alkanoyl, di($C_{1-4}$alkyl) amino$C_{1-4}$alkyl, $C_{1-4}$alkylamino$C_{1-4}$alkoxy, di($C_{1-4}$alkyl) amino$C_{1-4}$alkoxy, carboxy, carboxamido, trifluoromethyl, cyano, —C(O)NR$^{38}$R$^{39}$, —NR$^{40}$C(O)R$^{41}$ (wherein R$^{38}$, R$^{39}$, R$^{40}$ and R$^{41}$, which may be the same or different, each represents hydrogen, $C_{1-4}$alkyl, hydroxy$C_{1-4}$alkyl or $C_{1-3}$alkoxy$C_{2-3}$alkyl) and a group —(—O—)$_f$($C_{1-4}$alkyl)$_g$ ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);
10) —R$^g$R$^{33}$ (wherein R$^{33}$ is as defined hereinbefore);
11) —R$^h$R$^{33}$ (wherein R$^{33}$ is as defined hereinbefore);
12) —R$^i$R$^{33}$ (wherein R$^{33}$ is as defined hereinbefore);
13) —R$^j$X$^6$R$^{33}$ (wherein X$^6$ represents —O—, —C(O)—, —S—, —SO—, —SO$_2$—, —OC(O)—, —NR$^{38}$C(O)—, —C(O)NR$^{39}$—, —SO$_2$NR$^{40}$—, —NR$^{41}$SO$_2$— or —NR$^{42}$— (wherein R$^{38}$, R$^{39}$, R$^{40}$, R$^{41}$ and R$^{42}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
14) —R$^k$X$^7$R$^{33}$ (wherein X$^7$ represents —O—, C(O), —S—, —SO—, —SO$_2$—NR$^{43}$C(O)—, —C(O)NR$^{44}$—, —SO$_2$NR$^{45}$—, —NR$^{46}$SO$_2$— or —NR$^{47}$— (wherein R$^{43}$, R$^{44}$, R$^{45}$, R$^{46}$ and R$^{47}$ each independently represents hydrogen, $C_{1-3}$alkyl, hydroxy$C_{1-3}$alkyl or $C_{1-3}$alkoxy$C_{2-3}$ alkyl) and R$^{33}$ is as defined hereinbefore);
15) —R$^m$X$^8$R$^{33}$ (wherein X$^8$ represents —O—, —C(O)—, —S—, —SO—, —SO$_2$—, —NR$^{48}$C(O)—, —C(O) NR$^{49}$—, —SO$_2$NR$^{50}$—, —NR$^{51}$SO$_2$— or NR$^{52}$— (wherein R$^{48}$, R$^{49}$, R$^{50}$, R$^{51}$ and R$^{52}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
16) —R$^n$X$^9$R$^{n'}$R$^{33}$ (wherein X$^9$ represents —O—, —C(O)—, —S—, —SO—, —SO$_2$—, —NR$^{53}$C(O)—, —C(O)NR$^{54}$—, —SO$_2$NR$^{55}$—, —NR$^{56}$SO$_2$— or —NR$^{57}$— (wherein R$^{53}$, R$^{54}$, R$^{55}$, R$^{56}$ and R$^{57}$ each independently represents hydrogen, $C_{1-3}$alkyl, hydroxy$C_{1-3}$alkyl or $C_{1-3}$alkoxy$C_{2-3}$alkyl) and R$^{33}$ is as defined hereinbefore);
17) —R$^p$X$^9$—R$^{p1}$R$^{32}$ (wherein X$^9$ and R$^{32}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$ alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$ alkyl)amino, aminosulphonyl, N—$C_{1-4}$alkylaminosulphonyl and N,N-di($C_{1-4}$alkyl)aminosulphonyl;
20) —R$^t$X$^9$R$^{t'}$R$^{32}$ (wherein X$^9$ and R$^{32}$ are as defined hereinbefore);
21) —R$^u$X$^9$R$^{u'}$R$^{32}$ (wherein X$^9$ and R$^{32}$ are as defined hereinbefore); and
22) —R$^v$R$^{58}$(R$^{v'}$)$_q$(X$^9$)$_r$R$^{59}$(wherein X$^9$ is as defined hereinbefore, q is 0 or 1, r is 0 or 1 and R$^{58}$ is a $C_{1-3}$alkylene group or a cyclic group selected from cyclopropyl, cyclobutyl, cyclopentylene, cyclohexylene or a 5–6-membered saturated heterocyclic group with 1–2 heteroatoms, selected independently from O, S and N, which $C_{1-3}$alkylene group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$ alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$ alkoxy and a group —(—O—)$_f$($C_{1-4}$alkyl)$_g$ringD (wherein f is 0 or 1, g is 0 or 1 and ring D is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);and R$^{59}$ is hydrogen, $C_{1-3}$alkyl, or a cyclic group selected from cyclopropyl, cyclobutyl, cyclopentyl, cyclohexyl and a 5–6-membered saturated heterocyclic group with 1–2 heteroatoms, selected independently from O, S and N, which $C_{1-3}$alkyl group may bear 1 or 2 substituents selected from oxo, hydroxy, halogeno, $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$ alkoxy and a group —(—O—)$_f$($C_{1-4}$alkyl)$_g$ringD (wherein f is 0 or 1, g is 0 or 1 and ring D, is a cyclic group selected from $C_{3-6}$cycloalkyl, aryl or 5–6-membered saturated or unsaturated heterocyclic group with 1–2 heteroatoms, selected independently from O, S and N, which cyclic group may bear one or more substituents selected from halo and $C_{1-4}$alkyl);

and wherein $R^a$, $R^b$, $R^{b'}$, $R^c$, $R^{c'}$, $R^d$, $R^g$, $R^j$, $R^n$, $R^{n'}$, $R^p$, $R^{p'}$, $R^r$, $R^{u'}$, $R^v$ and $R^{v'}$ are independently selected from $C_{1-8}$alkylene groups optionally substituted by one or more substituents selected from hydroxy, halogeno, amino, $R^e R^h$, $R^k$ and $R^t$ are independently selected from $C_{2-8}$alkenylene groups optionally substituted by one or more substituents selected from hydroxy, halogen, amino, and $R^u$ may additionally be a bond; and $R^f$, $R^n$, $R^m$ and $R^u$ are independently selected from by $C_{2-8}$alkynylene groups optionally substituted by one or more substituents selected from hydroxy, halogeno, amino.

For instance, $R^1$, $R^2$, $R^3$, $R^4$ are independently selected from, halo, cyano, nitro, trifluoromethyl, $C_{1-3}$alkyl, —$NR^7R^8$ (wherein $R^7$ and $R^8$, which may be the same or different, each represents hydrogen or $C_{1-3}$alkyl), or other groups from formula —$X^1R^9$ (wherein $X^1$ represents a direct bond, —O—, —$CH_2$—, —OCO—, carbonyl, —S—, —SO—, —$SO_2$—, —$NR^{10}CO$—, —$CONR^{11}$—, —$SO_2NR^{12}$—, —$NR^{13}SO_2$— or —$NR^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following groups:

1') hydrogen or $C_{1-5}$alkyl which may be unsubstituted or which may be substituted with one or more groups selected from hydroxy, fluoro or amino, 2') $C_{1-5}$alkyl$X^2C(O)R^{15}$ (wherein $X^2$ represents —O— or —$NR^{16}$— (in which $R^{15}$ represents hydrogen, $C_{1-3}$alkyl or $C_{1-3}$alkoxy$C_{2-3}$alkyl) and $R^5$ represents $C_{1-3}$alkyl, —$NR^{17}R^{18}$ or —$OR^{19}$ (wherein $R^{17}$, $R^{18}$ and $R^{19}$ which may be the same or different each represents hydrogen, $C_{1-3}$alkyl or $C_{1-3}$alkoxy$C_{2-3}$alkyl));

3') $C_{1-5}$alkyl$X^3R^{20}$ (wherein $X^3$ represents —O—, —S—, —SO—, —$SO_2$—, —OCO—, —$NR^{21}CO$—, —$CONR^{22}$—, —$SO_2NR^{23}$—, —$NR^{24}SO_2$— or —$NR^{25}$— (wherein $R^{21}$, $R^{22}$, $R^{23}$, $R^{24}$ and $R^{25}$ each represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{26}$ (wherein $X^4$ and $X^5$ which may be the same or different are each —O—, —S—, —SO—, —$SO_2$—, —$NR^{27}CO$—, —$CONR^{28}$—, —$SO_2NR^{29}$—, —$NR^{30}SO_2$— or —$NR^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5') $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{32}$ (wherein $R^{32}$ is as defined in (5') above);
7') $C_{2-5}$alkenyl$R^{32}$ (wherein $R^{32}$ is as defined in (5') above);
8') $C_{2-5}$alkynyl$R^{32}$ (wherein $R^{32}$ is as defined in (5') above);
9') $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —$CONR^{34}R^{35}$ and —$NR^{36}COR^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl));

10') $C_{1-5}$alkyl$R^{33}$ (wherein $R^{33}$ is as defined in (9') above);
11') $C_{2-5}$alkenyl$R^{33}$ (wherein $R^{33}$ is as defined in (9') above);
12') $C_{2-5}$alkynyl$R^{33}$ (wherein $R^{33}$ is as defined in (9') above);
13') $C_{1-5}$alkyl$X^6R^{33}$ (wherein $X^6$ represents —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{33}$ is as defined hereinbefore);

14') $C_{2-5}$alkenyl$X^7R^{33}$ (wherein $X^7$ represents —O—, —S—, —SO—, —$SO_2$—, —$NR^{43}CO$—, —$CONR^{44}$—, —$SO_2NR^{45}$—, —$NR^{46}SO_2$— or —$NR^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15') $C_{2-5}$alkynyl$X^8R^{33}$ (wherein $X^8$ represents —O—, —S—, —SO—, —$SO_2$—, —$NR^{48}CO$—, —$C(O)NR^{49}$—, —$SO_2NR^{50}$—, —$NR^{51}SO_2$— or —$NR^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{33}$ is as defined hereinbefore);

16') $C_{1-3}$alkyl$X^9C_{1-3}$alkyl$R^{33}$ (wherein $X^9$ represents —O—, —S—, —SO—, —$SO_2$—, —$NR^{53}CO$—, —$C(O)NR^{54}$—, —$SO_2NR^{55}$—, —$NR^{56}SO_2$— or —$NR^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17') $C_{1-3}$alkyl$X^9C_{1-3}$alkyl$R^{32}$ (wherein $X^9$ and $R^{32}$ are as defined in (5') above); provided that least one of $R^2$ or $R^3$ is other than hydrogen.

Preferably $R^1$ is hydrogen. Suitably $R^4$ is hydrogen or a small substituent such as halo, $C_{1-4}$ alkyl or $C_{1-4}$alkoxy such as methoxy.

Preferably both $R^1$ and $R^4$ are hydrogen.

In a preferred embodiment, at least one group $R^2$ or $R^3$, preferably $R^3$, comprises a chain of at least 3 and preferably at least 4 optionally substituted carbon atoms or heteroatoms such as oxygen, nitrogen or sulphur. Most preferably the chain is substituted by a polar group which assists in solubility.

Suitably $R^3$ is a group $X^1R^9$.

Preferably in this case, $X^1$ is oxygen and $R^9$ includes a methylene group directly adjacent $X^1$. Preferably where bridging alkylene, alkenylene or alkynylene groups $R^a$, $R^b$, $R^{b'}$, $R^c$, $R^{c'}$, $R^d$, $R^g$, $R^j$, $R^n$, $R^{n'}$, $R^p$, $R^{p'}$, $R^r$, $R^{u'}$, $R^v$, $R^{v'}$, $R^eR^h$, $R^kR^t$, $R^f$, $R^i$, $R^m$ and $R^u$ are present, at least one such group includes a substituent and in particular a hydroxy substituent.

In particular $R^9$ is selected from a group of formula (1), (3), (6) or (10) above and preferably selected from groups (1) or (10) above. Particular groups $R^9$ are those in group (1) above, especially alkyl such as methyl or halo substituted alkyl, or those in group (10) above. In one suitable embodiment, at least one of $R^2$ or $R^3$ is a group $OC_{1-5}$alkyl$R^{33}$ and $R^{33}$ is a heterocyclic ring such as an N-linked morpholine ring such as 3-morpholinopropoxy.

Other preferred groups for R³ are groups of formula (3) above in particular those where X³ is NR²⁵.

Suitably R² is selected from, halo, cyano, nitro, trifluoromethyl, $C_{1-3}$alkyl, —NR⁷R⁸ (wherein R⁷ and R⁸, which may be the same or different, each represents hydrogen or $C_{1-3}$alkyl), or a group —X¹R⁹. Preferred examples of —X¹R⁹ for R² include those listed above in relation to R³.

Other examples for R² and R³ include methoxy or 3,3,3-trifluoroethoxy.

Suitably R⁵ is optionally substituted pyridine or optionally substituted pyrimidine and is preferably optionally substituted pyrimidine.

Most preferably, R⁵ is a substituted pyridine or substituted pyrimidine group. Suitably, at least one substituent is positioned at the para position on the ring R⁵. Thus suitable groups R⁵ include compounds of sub-formulae Most preferably, R⁵ is a substituted pyridine or substituted pyrimidine group. Suitably, at least one substituent is positioned at the para position on the ring R⁵. Thus suitable groups R⁵ include compounds of sub-formulae

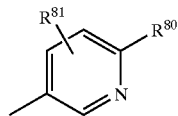

(i)

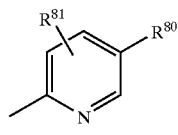

(ii)

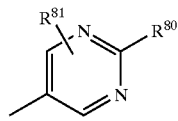

(iii)

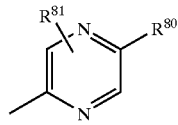

(iv)

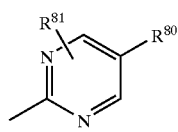

(v)

wherein R⁸⁰ is a substituent group and in particular R⁸⁰ is a large substituent of a chain of at least 4 atoms, in particular a group of sub-formula (II), (f) or sub-formula (VI) as defined below, and R⁸¹ is hydrogen or a substituent and in particular a small substituent such as halo, $C_{1-4}$alkoxy such as methoxy, or othoxy, cyano or trifluoromethyl, or phenyl;

Suitable substituents for the pyridine or pyrimidine groups R⁵ include a functional group as defined above; hydrocarbyl optionally substituted by one or more functional groups as defined above; heterocyclyl optionally substituted by one or more functional groups or hydrocarbyl groups wherein the hydrocarbyl group may be substituted by a functional group or a heterocyclic group as defined above; alkoxy optionally substituted by a functional group, or a heterocylic group which is optionally substituted by a functional group.

In particular, R⁵ is substituted by one or more groups selected from halo,$C_{1-4}$alkyl, optionally substituted $C_{1-6}$ alkoxy, $C_{1-4}$alkoxymethyl, di($C_{1-4}$alkoxy)methyl, $C_{1-4}$alkanoyl, trifluoromethyl, cyano, amino, $C_{2-5}$-alkenyl, $C_{2-5}$alkynyl, a phenyl group, a benzyl group or a 5–6-membered heterocyclic group with 1–3 heteroatoms, selected independently from O, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl.

Other substituents groups for R⁵ include carboxamido, carboxy and benzoyl.

Suitably R⁵ is substituted with at least one group which has at least 4 atoms which may be carbon or heteroatoms forming a chain. A particular example of such a substituent is optionally substituted alkoxy. Suitable substituents for the alkoxy group include those listed above in relation to R⁷⁷, R⁷⁸ and R⁷⁹.

A further particular substituent group for R⁵ is a group of sub-formula (II)

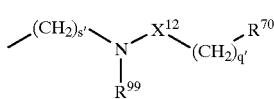

(II)

where q' is 0, 1, 2, 3 or 4;
s' is 0 or 1;
X¹² is C(O) or S(O₂), and preferably C(O);
R⁷⁰ is hydrogen, hydroxy, $C_{1-6}$alkyl, $C_{1-6}$alkoxy, amino, N—$C_{1-6}$alkylamino,
N,N-($C_{1-6}$alkyl)₂amino, hydroxy$C_{2-6}$alkoxy, $C_{1-6}$alkoxy$C_{2-6}$alkoxy, amino$C_{2-6}$alkoxy,
N—$C_{1-6}$alkylamino$C_{2-6}$alkoxy, N,N-($C_{1-6}$alkyl)₂amino$C_{2-6}$alkoxy or $C_{3-7}$cycloalkyl,
or R⁷⁰ is of the Formula (III):

-K-J    (III)

wherein J is aryl, heteroaryl or heterocyclyl and K is a bond, oxy, imino, N—($C_{1-6}$alkyl)imino, oxy$C_{1-6}$alkylene, imino$C_{1-6}$alkylene, N—($C_{1-6}$alkyl)imino$C_{1-6}$alkylene, —NHC(O)—, —SO₂NH—, —NHSO₂— or —NHC(O)—$C_{1-6}$alkylene-, and any aryl, heteroaryl or heterocyclyl group in a R⁷⁰ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)ₙ— (wherein n is 0–2), N—$C_{1-6}$alkylamino, N,N-($C_{1-6}$alkyl)₂ amino, $C_{1-6}$alkoxycarbonyl, N—$C_{1-6}$alkylcarbamoyl, N,N-($C_{1-6}$alkyl)₂carbamoyl, $C_{2-6}$alkanoyl, $C_{1-6}$alkanoyloxy, $C_{1-6}$alkanoylamino, N—$C_{1-6}$ alkylsulphamoyl, N,N-($C_{1-6}$alkyl)$_2$sulphamoyl, $C_{1-6}$alkylsulphonylamino and $C_{1-6}$alkylsulphonyl-N—($C_{1-6}$alkyl)amino, and suitably also oxo, or any aryl, heteroaryl or heterocyclyl group in a $R^{70}$ group may be optionally substituted with one or more groups of the Formula (IV):

wherein $A^1$ is halo, hydroxy, $C_{1-6}$alkoxy, cyano, amino, N—$C_{1-6}$alkylamino, N,N-($C_{1-6}$alkyl)$_2$amino, carboxy, $C_{1-6}$alkoxycarbonyl, carbamoyl, N—$C_{1-6}$alkylcarbamoyl or N,N-($C_{1-6}$alkyl)$_2$carbamoyl, p is 1–6, and $B^1$ is a bond, oxy, imino, N—($C_{1-6}$alkyl)imino or —NHC(O)—, with the proviso that p is 2 or more unless $B^1$ is a bond or —NHC(O)—;

or any aryl, heteroaryl or heterocyclyl group in a $R^{70}$ group may be optionally substituted with one or more groups of the Formula (V):

wherein $D^1$ is aryl, heteroaryl or heterocyclyl and $E^1$ is a bond, $C_{1-6}$alkylene, oxy$C_{1-6}$alkylene, oxy, imino, N—($C_{1-6}$alkyl)imino, imino$C_{1-6}$alkylene, N—($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N—($C_{1-6}$alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a substituent on $R^4$ may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N—($C_{1-6}$alkyl)$_2$carbamoyl, $C_{2-6}$alkanoyl, amino, N—$C_{1-6}$alkylamino and N,N-($C_{1-6}$alkyl)$_2$amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N—$C_{1-6}$alkylamino, N,N-($C_{1-6}$alkyl)$_2$amino and heterocyclyl;

and $R^{99}$ is hydrogen or a group C(O)$R^{70}$ where $R^{70}$ is as defined above and is preferably hydrogen.

In yet a further alternative, $R^{70}$ may be cycloalkenyl or cycloalkynyl such as cyclohexenyl, alkenyl optionally substituted by aryl such as styryl or alkyl substituted by cycloalkenyl such as cyclohexenylethyl Suitably, when q' is 0, $R^{70}$ is other than hydroxy.
Preferably s' is 0.
Preferably the group of sub-formula (II) is a group of sub-formula (IIA)

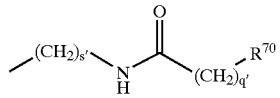

where s', q' and $R^{70}$ are as defined above.
A preferred example of a substituent of formula (II) or (IIA) is a group where q' is 0.
Examples of heterocyclyl groups for $R^{70}$ include pyridyl, methyledioxyphenyl, furyl, pyrrolyl, thiophene, quinolyl, isoquinolyl, thiazolyl, thiadiazolyl, pyrazolyl, tetrahydrothiophene-1,1-dioxide, dioxan, tetrahydrofuryl, pyrazinyl, imidazolyl, tetrahydropyran, indolyl, indanyl, pyrrolidine, or isoxazolyl.

A particular example of a group $R^{70}$ in formula (II) is phenyl. Preferably $R^{70}$ is halosubstituted phenyl and 2-chloro4-fluorophenyl is a particularly preferred example.

More suitably $R^5$ is substituted by a group —$X^{10}$(CH$_2$)$_{p'}$, —$X^{11}R^{100}$ or —$X^{13}R^{100}$ where p' is 1–3, $X^{10}$ and $X^{11}$ are independently selected from a bond, —O—, —S— or $NR^{101}$—where $R^{101}$ is hydrogen or a $C_{1-3}$alkyl, provided that one of $X^{10}$ or $X^{11}$ is a bond; $X^{13}$ is —O—, —S— or $NR^{102}$— where $R^{102}$ is hydrogen or a $C_{1-4}$alkyl and $R^{100}$ is hydrogen or optionally substituted hydrocarbyl or optionally substituted heterocycyl. Suitable optional substituents for hydrocarbyl and heterocyclyl groups $R^{100}$ include functional groups as defined above. Preferred groups $R^{100}$ are hydrocarbyl or heterocyclyl groups which are included in the definition of $R^{70}$ as defined hereinbefore. Preferably one of $X^{10}$ or $X^{11}$ is other than a bond.

Particular examples of $R^{70}$ in this instance include optionally substituted phenyl and especially, mono or di-halophenyl,or optionally substituted pyridyl such as nitropyridyl.

Another preferred substituent group for $R^5$ is a group of formula (VI)

where $R^{71}$ and $R^{72}$ are independently selected from hydrogen or $C_{1-4}$alkyl, or $R^{71}$ and $R^{72}$ together form a bond, and $R^{73}$ is a group $OR^{74}$, $NR^{75}R^{76}$ where $R^{74}$, $R^{75}$ and $R^{76}$ are independently selected from optionally substituted hydrocarbyl or optionally substituted heterocyclic groups, and $R^{75}$ and $R^{76}$ may additionally form together with the nitrogen atom to which they are attached, an aromatic or non-aromatic heterocyclic ring which may contain further heteroatoms.

Suitable optional substituents for hydrocarbyl or heterocyclic groups $R^{74}$, $R^{75}$ and $R^{76}$ include functional groups as defined above. Heterocyclic groups $R^{74}$, $R^{75}$ and $R^{76}$ may further be substituted by hydrocarbyl groups.

In particular, $R^{71}$ and $R^{72}$ in sub-formula (VI) are hydrogen.

Particular examples of $R^{73}$ are groups $OR^{74}$ where $R^{74}$ is $C_{1-4}$alkyl.

Further examples of $R^{73}$ are groups of formula $NR^{77}R^{76}$ where one of $R^{75}$ or $R^{76}$ is hydrogen and the other is optionally substituted $C_{1-6}$alkyl, optionally substituted aryl or optionally substituted heterocyclyl.

In particular, one of $R^{75}$ or $R^{76}$ is hydrogen and the other is $C_{1-6}$alkyl optionally substituted with trifluoromethyl, $C_{1-3}$ alkoxy such as methoxy, cyano, thio$C_{1-4}$alkyl such as methylthio, or heterocyclyl optionally substituted with hydrocarbyl, such as indane, furan optionally substituted with $C_{1-4}$ alkyl such as methyl.

In another embodiment, one of $R^{75}$ or $R^{76}$ is hydrogen and the other is an optionally substituted heterocyclic group such as pyridine, or a phenyl group optionally substituted with for example one or more groups selected from halo, nitro, alkyl such as methyl, or alkoxy such as methoxy.

Other suitable substituents groups for $R^5$ are groups of sub-formula (VII)

(VII)

where p" is 0 or 1 and $R^{83}$ and $R^{84}$ are independently selected from hydrogen, optionally substituted hydrocarbyl or optionally substituted heterocyclyl, or $R^{83}$ and $R^{84}$ together with the nitrogen atom to which they are attached form an optionally substituted heterocyclic ring. Suitable optional substituents for hydrocarbyl or heterocyclic groups $R^{83}$ and $R^{84}$ include functional groups as defined above and heterocyclic groups $R^{83}$ or $R^{84}$ may further be substituted by a hydrocarbyl group.

Examples of groups for $R^{83}$ and $R^{84}$ include $C_{1-4}$alkyl substituted by cycloalkyl such as 2-cyclopropylethyl; $C_{1-6}$alkylthio such a methylthio; $C_{1-6}$alkoxy; or a group —$(CH_2)_qR^{70}$ where q and $R^{70}$ are as defined above in relation to formula (II).

Suitably one of $R^{83}$ or $R^{84}$ is hydrogen, or methyl, ethyl or propyl optionally substituted with hydroxy and preferably one of $R^{83}$ or $R^{84}$ is hydrogen. In this case, the other is suitably a larger substituent for example of at least 4 carbon or heteroatoms, and is optionally substituted hydrocarbyl or optionally substituted heterocyclyl. Particular optionally substituted hydrocarbyl groups for $R^{83}$ or $R^{84}$ include alkyl, cycloalkyl, alkenyl, or aryl any of which is optionally substituted with a functional group as defined above, or in the case of aryl groups, with an alkyl group and in the case of alkyl group, with an aryl or heterocyclic group either of which may themselves be optionally substituted with alkyl or a functional group. Examples of optionally substituted aryl groups $R^{83}$ or $R^{84}$ include phenyl optionally substituted with one or more groups selected from $C_{1-6}$ alkyl group such as methyl or ethyl (either of which may be optionally substituted with a functional group such as hydroxy); or a functional group as defined above (such as halo like fluoro, chloro cr bromo, hydroxy, alkoxy such as methoxy, trifluoromethyl, nitro, cyano, trifluromethoxy, $CONH_2$, $C(O)CH_3$, amino, or dimethylamino).

When $R^{83}$ or $R^{84}$ is an optionally substituted alkyl group, it is suitably a $C_{1-6}$alkyl group, optionally substituted with one or more functional groups (such as cyano, hydroxy, alkoxy in particular methoxy or ethoxy, alkylthio in particular methylthio, COOalkyl such as $COOCH_3$), or aryl optionally substituted with a functional group as defined above (in particular in relation to $R^{83}$ or $R^{84}$ themselves, or an optionally substituted heterocyclic group such as N-methyl pyrrole.

When $R^{83}$ and $R^{84}$ is optionally substituted cycloalkyl, it is suitable cyclohexyl optionally substituted with a functional group such as hydroxy.

When $R^{83}$ and $R^{84}$ is optionally substituted alkenyl, it is suitably prop-2-enyl.

When $R^{83}$ or $R^{84}$ is optionally substituted heterocyclyl, or $R^{83}$ and $R^{84}$ together form a heterocyclic group, then this may be aromatic or non-aromatic and includes in particular, piperadine, piperazine, morpholino, pyrrolidine or pyridine any of which may be optionally substituted with a functional group such as hydroxy, alkoxy such as methoxy, or alkyl such as methyl which may itself be substituted with for instance a hydroxy group.

Where possible, the group $R^5$ may have a second substituent in particular halo, $C_{1-4}$alkoxy such as methoxy, or ethoxy, cyano, trifluoromethyl, or phenyl. Preferably any second substituent is a small group.

Most preferably, in the compound of formula (I), at least one substituent is positioned at the para position on the pyrimidine ring. Thus preferably the compound of formula (I) incorporates a further group of sub-formulae (vi and vii):

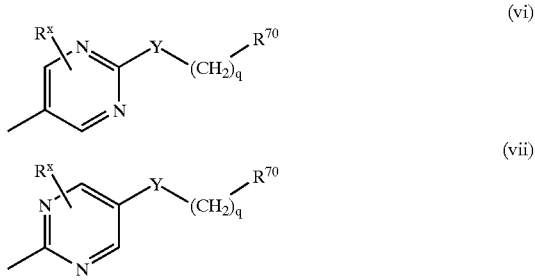

wherein $R^x$ is hydrogen, halo, $C_{1-4}$alkoxy, cyano, trifluoromethyl, or phenyl; Where $R^x$ is other than hydrogen, it is preferably a small group such as halo, chloro, flouro, methoxy, ethoxy cyano, or trifloruomethyl;

Y is a group —$NR^6C(O)$—, —$C(O)NR^6$—, —$NR^6S(O)_2$—, —$NHR^6$—, —$NR^6CH=N$—, —$C(=NR^6)NR^{6'}$—, —$NR^6C(=NR^{6'})NR^{6''}$—, —$C(O)$, —$CH=CHC(O)NR^6$—, —$C\equiv CC(O)NR^6$, —$CH=CH$—, —$C\equiv C$—, —$S$—, —$S(O)$—, —$S(O)_2$—, or —$O$— where $R^6$, $R^{6'}$ and $R^{6''}$ are independently selected from hydrogen or $C_{1-4}$alkyl.

Preferably, Y is a group —$NR^6C(O)$—, —$C(O)NR^6$—, —$NR^6S(O)_2$—, —$NHR^6$—, —$NR^6CH=N$—, —$C(=NR^6)NR^{6''}$—, —$NR^6C(=NR^{6'})NR^{6''}$—, —$CH=CHC(O)NR^6$—, —$C\equiv CC(O)NR^6$, —$CH=CH$—, —$C\equiv C$—, —$S$— or —$S(O)$—.

Most preferably, Y is a group —$NR^6C(O)$— or —$C(O)NR^6$— and most preferably Y is —$NR^6C(O)$—.

q is 0 or an integer of from 1 to 6;

Suitably, when Y is $C(O)$, —$S(O)_2$—, or —$O$—, either q is other than 0 or $R^{70}$ is other than unsubstituted phenyl.

$R^{70}$ is as defined in relation to Sub Formulae (iv) above.

Preferably, $R^5$ is a group of sub-formula (vi) or (vii) as defined above, and most preferably is a group of sub-formula (vi).

A particular example of a compound of Formula (I) is a compound of Formula (VIII)

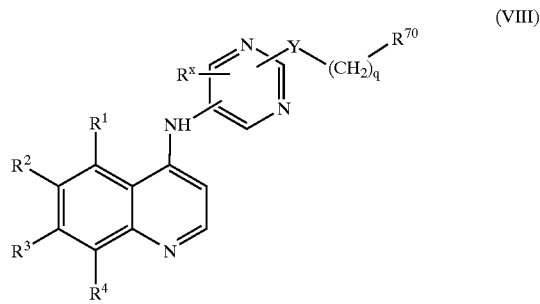
(VIII)

Wherein $R^1$, $R^2$, $R^3$, $R^4$, $R^x$, Y, q and $R^{70}$ are as defined above.

A particular example of a compound of formula (I) is a compound of formula (IX)

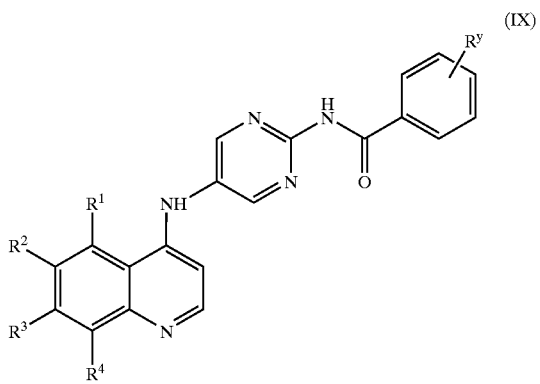

where $R^1$, $R^2$, $R^3$ and $R^4$ are as defined above and $R^y$ is hydrogen or halogen.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. There may be more than one cation or anion depending on the number of charged functions and the valency of the cations or anions. Where the compound of formula (I) includes an acid functionality, salts may be base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. A preferred pharmaceutically acceptable salt is a sodium salt.

An in vivo hydrolyzable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include $C_{1-6}$alkyl esters such as methyl or ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxy-carbonyloxy$C_{1-6}$alkyl esters for example 1-cyclohexylcarbonyloxyethyl;
1,3-dioxolen-2-onylmethyl esters for example 5-methyl-1,3-dioxolen-2-onylmethyl; and
$C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Suitable amides are derived from compounds of formula (I) which have a carboxy group which is derivatised into an amide such as a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

Esters which are not in vivo hydrolysable may be useful as intermediates in the production of the compounds of formula (I).

Particular examples of compounds of formula (I) are set out in Table 1

TABLE I

| Compound No. | $R^1$ | $R^2$ | $R^3$ | (structure) |
|---|---|---|---|---|
| 1 | H | CN | | —O—CH₂CH₂CH₂—N(morpholine) |
| 2 | H | OCH₃ | | —O—CH₂CH₂CH₂—N(morpholine) |
| 3 | H | H | | —O—CH₂CH₂—N(triazole) |
| 4 | H | H | | —O—CH₂CH₂CH₂—N(morpholine) |
| 5 | H | H | OCH₂CH₂OCH₃ | |
| 6 | H | H | OCH₂CH₂OCH₂CH₂OCH₃ | |
| 7 | H | NHCOCH₃ | H | |
| 8 | Cl | H | H | |
| 9 | H | CN | H | |
| 10 | CH₃ | H | CH₃ | |
| 11 | H | H | Cl | |
| 12 | H | H | H | |
| 13 | H | H | CF₃ | |
| 14 | H | CF₃ | H | |

Compounds of formula (I) may be prepared by various methods which would be apparent from the literature. For example compounds of formula (I) may be prepared by reacting a compound of formula (X)

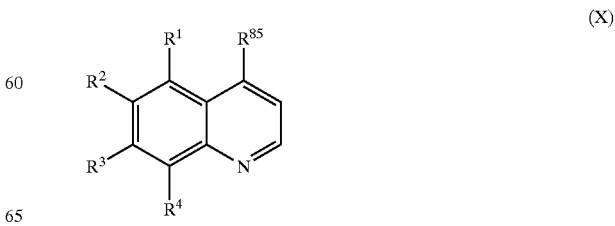

where $R^1$, $R^2$, $R^3$, and $R^4$ are as defined in relation to formula (I) and $R^{85}$ is a leaving group, with a compound of formula (XI)

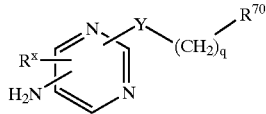

(XI)

where $R^a$, Y, q and $R^{70}$ are as defined in relation to formula (I). Suitable leaving groups for $R^{85}$ include halo such as chloro, mesylate and tosylate. The reaction is suitably effected in an organic solvent such as an alcohol like pentanol or isopropanol, at elevated temperatures, conveniently at the reflux temperature of the solvent.

Compounds of formula (X) and (XI) are either known compounds or they can be derived from known compounds by conventional methods.

Compounds of formula (XI) may be prepared by reduction of a compound of formula (XII)

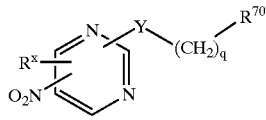

(XII)

for example by reaction with hydrogen in the presence of a catalyst such as a platinum or palladium catalyst or by reaction with a reducing agent such as sodium hydrosulphite.

Compounds of formula (XII) can for example, be derived from compounds of formula (XIII)

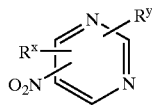

(XIII)

where $R^x$ is as defined hereinbefore and $R^y$ is amino, carboxy, halo, alkylketone, aldehyde, nitrile, mercapto, or hydroxy using routes set out in the literature. For example, where Y is —$NR^6C(O)$— or —$NR^6S(O)_2$—, the compound of formula (XII) can be derived from compounds of formula (XIV)

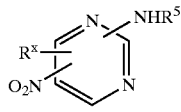

(XIV)

where $R^x$ and $R^6$ are as defined in relation to formula (I), by reaction with a compound of formula (XV)

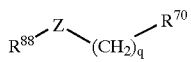

(XV)

where q and $R^{70}$ are as defined in relation to formula (I), Z is a bond, C(O) or S(O), and $R^{88}$ is a leaving group such as halo or aryloxy. The reaction is suitably effected in the presence of a base such as pyridine at elevated temperatures, conveniently at the reflux temperature of the solvent.

Similarly, compounds of formula (XII) where Y is —C(O)$NR^6$— may be prepared from compound of formula (XVI)

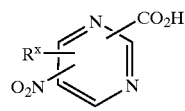

(XVI)

where $R^x$ is as defined in relation to formula (I), using conventional amidation methods with the appropriate amine. Compounds of formula (XVI) are either known compounds or they may be prepared by hydrolysis of compounds of formula (XVII)

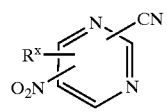

(XVII)

where $R^x$ is as defined above.

Compounds of formula (XII) where Y is an acetylene group of formula —C≡C— may be prepared by reduction of the nitrile of formula (XVII) for example, with di-isobutylaluminium hydride to give the corresponding aldehyde, which can then be reacted for example with phosphorus ylids would give compounds of formula (XII) where Y is —C≡C—. Reaction of nitrile (XVII) with alkyl- or aryl lithiums would give ketones of formula (XII) where Y=C(O)—.

Nitriles of formula (XVII) can be made from a compound of formula (XIII) where $R^y$ is a sulphide by oxidation with a peracid such as meta-chlorobezoic acid to form the corresponding sulphone and reaction of this product with potassium cyanide in a solvent such as N-methylpyrrolidine.

Where in the compound of formula (X), a substitutent such as $R^3$ is a particularly complex substituent, it may be introduced by reacting a compound of formula (XIII)

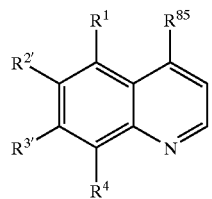

(XVIII)

where $R^1$ and $R^4$ are as defined in relation to formula (I), $R^{85}$ is as defined in relation to formula (X), one of $R^{2'}$ or $R^{3'}$ is equivalent to $R^2$ or $R^3$ as defined in relation to formula (I), and the other is hydroxy; with a compound of formula (XVIII)

H—X—$R^9$ (XIX)

where X is as defined in relation to formula (I) and is preferably oxygen, and $R^9$ is as defined in relation to formula (I). The reaction is suitably effected in the presence of dehydrating reagents such as diethyl azodicarboxylate and triphenylphosphine. It is carried out in for example, an organic such as dichloromethane, preferably at moderate temperatures, for example of from 0 to 50° C. and conveniently at ambient temperature.

Compounds of formula (I) are inhibitors of aurora 2 kinase. As a result, these compounds can be used to treat disease mediated by these agents, in particular proliferative disease.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of proliferative disease such as cancer and in particular cancers such as colorectal or breast cancer where aurora 2 is upregulated.

According to a further aspect of the present invention there is provided a method for inhibiting aurora 2 kinase in a warm blooded animal, such as man, in need of such treatment, which comprises administering to said animal an effective amount of a compound of formula (I), or a pharmaceutically acceptable salt, or an in vivo hydrolysable ester thereof.

The invention also provides a pharmaceutical composition comprising a compound of formula (I) as defined herein, or a pharmaceutically acceptable salt, or an an in vivo hydrolysable ester thereof, in combination with at pharmaceutically acceptable carrier. Preferred compounds of formula (I) for use in the compositions of the invention are as described above.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring-agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of aurora 2 kinase.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

A further aspect of the invention comprises a compound of formula (I) as defined above, or a pharmaceutically acceptable salt or in vivo hydrolysable ester thereof, for use in the preparation of a medicament for the treatment of proliferative disease. Preferred compounds of formula (I) for this purpose are as described above.

The following Examples illustrate the invention.

EXAMPLE 1

Preparation of Compound No. 1 in Table 1

Hydrochloric acid (0.05 ml of a 6.2 N solution in isopropanol) was added to a solution of 4-chloro-6-cyano-7-(3-morpholinopropoxy)quinoline (110 mg, 0.33 mmol) and 2-(N-benzoyl)2,5-diaminopyrimidine (85 mg, 0.40 mmol) in 2-pentanol (5 ml) and the mixture heated, at 120° C. for 6 hours. The reaction mixture was cooled to ambient temperature, diluted with ethyl acetate (25 ml), and the solid which precipitated was collected by suction filtration and washed with ethyl acetate. Purification by flash chromatography on silica gel, eluting with 5–20% methanol in dichloromethane yielded the title compound (100 mg, 59%) as a white solid:

$^1$H NMR (DMSOd$_6$, trifluoroacetic acid) 9.28 (s, 1H), 8.90 (s, 2H), 8.62 (d, 1H), 8.01 (d, 2H), 7.60 (m, 2H), 7.52 (t, 2H), 7.01 (d, 1H), 4.41 (m, 2H), 4.01 (d, 2H), 3.75 (t, 2H), 3.54 (d, 2H), 3.35 (t, 2H), 3.16 (t, 2H), 2.48 (m, 2H): MS (−ve ESI): 510 (M−H)$^-$.

4-Chloro-6-cyano-7-(3-morpholinopropoxy)quinoline and 2-(N-benzoyl) 2,5-diaminopyrimidine, used as the starting materials, were obtained as follows:

a) A mixture of 4-chloro-6-cyano-7-hydroxyquinoline (0.82 g, 4.0 mmol) in dichloromethane (25 ml) and N-(3-hydroxypropyl)morpholine (0.88 g, 6.0 mmol) was treated with diethyl azodicarboxylate (1.58 ml, 8.0 mmol) and triphenylphosphine (2.1 g, 8.0 mmol) for 1 hour at ambient temperature. Purification of the crude product by flash chromatography on silica gel, eluting with 5–10% methanol in 1:1 ethyl acetate/dichloromethane yielded the title compound (1.10 g, 69%) as a white solid:

$^1$H-NMR (DMSOd$_6$): 8.89 (d, 1H), 8.66 (s, 1H), 7.72 (d, 1H), 7.69 (s, 1H), 4.35 (t, 2H), 3.58 (m, 4H), 2.51 (t, 2H), 2.38 (m, 4H), 2.01 (m, 2H): MS (+ve ESI): 332 (M+H)$^+$.

b) Benzoyl chloride (0.92 ml, 7.93 mmol) was added dropwise to a stirred solution of 2-amino-5-nitropyrimidine (1.00 g, 7.14 mmol) in pyridine (20 ml) and the reaction was heated at reflux for 4 hours under an inert atmosphere. The reaction was allowed to cool to ambient temperature, poured into water (200 ml) and allowed to stand for 16 hours. The solid was collected by suction filtration, washed with water (3×20 ml) and dried in vacuo. An oily residue on the surface of the aqueous phase was dissolved in dichloromethane (50 ml) and then purified by flash chromatography on silica gel, eluting with 1–3% methanol. The two materials were identical and yielded 2-(N-benzoyl) 2-amino-5-nitropyrimidine (826 mg, 47% yield) as a white solid:

$^1$H-NMR (DMSO d$_6$): 11.73 (s, 1H), 9.43 (s, 1H), 7.96 (d, 2H, J=8 Hz), 7.47–7.65 (m, 3H): MS (+ve ESI): 243 (M−H)$^{30}$, MS (+ve ESI): 245 (M+H)$^+$.

c) 10% Platinum on carbon (71 mg, 0.036 mmol) was added to a solution 2-(N-benzoyl) 2-amino-5-nitropyrimidine (733 mg, 3.00 mmol) in ethanol (100 ml) at ambient temperature and the reaction stirred for 1 hour under an atmosphere of hydrogen. The reaction was filtered through a pad of celite and the solvents were evaporated in vacuo. Purification by flash chromatography on silica gel, eluting with 5% methanol in dichloromethane yielded 2-(N-benzoyl) 2,5-diaminopyrimidine (91 mg, 14% yield) as white solid:

$^1$H-NMR (DMSO d$_6$): 8.63 (s, 1H), 8.14 (s, 2H), 7.90 (d, 2H, J=8 Hz), 7.42–7.56 (m, 3H), 3.76 (s, 1H): MS (+ve ESI): 213 (M+H)$^+$, MS (+ve ESI): 215 (M+H)$^-$.

d) In an alternative procedure, a solution of 2-amino-5-nitropyrimidine (15.0 g, 107 mmol) and benzoic anhydride (48 g, 214 mmol) in diphenyl ether (53 g) was heated at 160° C. for 5 hours. The reaction was cooled to 90° C., t-butyl methyl ether (200 ml) was added and the reaction allowed to cool to ambient temperature. Collection of the solid by suction filtration, followed by washing with diethyl ether and drying in vacuo, yielded 2-(N-benzoyl) 2-amino-5-nitropyrimidine (22.4 g, 86% yield) as a white solid.

Platinum dioxide (2.0 g of a 10% w/w slurry) was added to a solution of 2-(N-benzoyl) 2-amino-5-nitropyrimidine (22.4 g, 92 mmol) in a mixture of ethyl acetate (200 ml) and ethanol (200 ml) and the reaction stirred under a hydrogen atmosphere (2 atmospheres pressure) for 2 hours at ambient temperature. The reaction was purged, the catalyst was filtered off and the solvents were removed in vacuo. Purification of the crude product by flash chromatography on silica gel, eluting with 5–10% methanol in dichloromethane yielded the title compound (15.6 g, 80%) as a white solid.

EXAMPLE 2

Preparation of Compound No. 2 in Table 1

An analogous reaction to that described in example 1, but starting with 4-chloro-6-methoxy-7-(3-morpholinopropoxy)quinoline (112 mg, 0.33 mmol), yielded the title compound (72 mg, 42%) as a white solid after flash chromatography on silica gel, eluting with 5–20% methanol in 1:1 ethyl acetate/dichloromethane:

$^1$H-NMR (DMSOd$_6$, trifluoroacetic acid): 8.94 (s, 2H), 8.48 (d, 1H), 8.16 (s, 1H), 8.02 (d, 2H), 7.53 (m, 4H), 6.92 (d, 1H), 4.33 (t, 2H), 4.03 (m, 5H), 3.78 (t, 2H), 3.55 (d, 2H) 3.35 (t, 2H), 3.17 (m, 2H), 2.49 (m, 2H) MS (+ve ESI): 515 (M+H)$^+$.

4-Chloro-6-methoxy-7-(3-morpholinopropoxy)quinoline, used as the starting material, was obtained as follows:

A mixture of 4-chloro-6-methoxy-7-hydroxy quinoline (0.63 g, 3.0 mmol) and N(3-hydroxypropyl)morpholine (0.54 g, 3.8 mmol) was treated with diethyl azodicarboxylate (1.38 g, 6.0 mmol) and triphenylphosphine (1.57 g, 6.0 mmol) at room temperature for 2 hours. Purification by flash chromatography on silica gel, eluting with 0–20% methanol in 1:1 ethyl acetate/dichloromethane yielded 4-Chloro-6-methoxy-7-(3-morpholinopropoxy)-quinoline (0.70 g, 69% yield) as white solid:

$^1$H-NMR (DMSOd$_6$): 7.56 (d, 1H), 7.46 (s, 1H), 7.39 (s, 1H), 4.22 (t, 2H), 4.02 (s, 3H), 3.59 (t, 4H), 2.47 (t, 2H), 2.39 (m, 4H), 1.98 (m, 2H).

EXAMPLE 3

Preparation of Compound 3 in Table 1

An analogous reaction to that described in example 1, but starting with 4-chloro-7-(2-(1,2,4 triazolo)ethoxy)quinoline (110 mg, 0.40 mmol), yielded the title compound (130 mg, 72%) as a white solid after flash chromatography on silica gel, eluting with 5–15% methanol in 1:1 ethyl acetate/dichloromethane:

$^1$H-NMR (DMSOd$_6$, TFA): 9.30 (s, 1H), 8.92 (s, 2H), 8.64 (d, 1H), 8.55 (d, 1H), 8.50 (s, 1H), 8.02 (d, 2H), 7.53 (m, 5H), 6.91 (d, 1H), 4.84 (t, 2H), 4.66 (t, 2H): MS (+ve ESI): 453 (M+H)$^+$.

EXAMPLE 4

Preparation of Compound 4 in Table 1

An analogous reaction to that described in example 1, but starting with 4-chloro-7-(3-morpholinopropoxy)quinoline (0.107 g, 0.35 mmol) and heating the reaction at 80° C. for 2 hours, yielded the title compound (78 mg, 46%) as a white solid after flash chromatography on silica gel, eluting with 5–15% methanol in 1:1 ethyl acetate/dichloromethane:

$^1$H-NMR (DMSOd$_6$, trifluoroacetic acid): 8.92 (s, 2H), 8.68 (d, 1H), 8.55 (d, 1H), 8.01 (d, 2H), 7.57 (m, 5H), 6.90 (d, 1H), 4.32 (t, 2H), 4.01 (d, 2H), 3.79 (t, 2H), 3.53 (d, 2H), 3.38 (m, 2H), 3.15 (m, 2H), 2.33 (m, 2H) MS (+ve ESI): 485 (M+H)$^+$.

EXAMPLE 5

Preparation of Compound 5 in Table 1

An analogous reaction to that described in example 1, but starting with 4-chloro-7-(2-methoxyethoxy)quinoline (0.107 g, 0.45 mmol) and heating for 3 hours, yielded the title compound (35 mg, 19%) as a white solid after flash chromatography on silica gel, eluting with 5–10% methanol in 1:1 ethyl acetate/dichloromethane:

$^1$H-NMR (DMSOd$_6$, trifluoroacetic acid): 8.83 (s, 2H), 8.51 (d, 1H), 8.45 (d, 1H), 7.93 (d, 2H), 7.54 (t, 1H), 7.45 (m, 3H), 7.31 (d, 1H), 6.80 (d, 1H), 4.26 (m, 2H), 3.69 (m, 2H), 3.26 (s, 3H): MS (+ve ESI): 416 (M+H)$^+$.

EXAMPLE 6

Preparation of Compound 6 in Table 1

An analogous reaction to that described in example 1, but starting with 4-chloro-7-(2-(2-methoxyethoxy)ethoxy)quinoline (0.112 g, 0.4 mmol) and heating for 3 hours, yielded the title compound (30 mg, 16%) as a white solid after flash chromatography on silica gel, eluting with 5–10% methanol in 1:1 ethyl acetate/dichloromethane:

$^1$H-NMR (DMSOd$_6$, trifluoroacetic acid): 8.90 (s, 2H), 8.59 (d, 1H), 8.52 (d, 1H), 8.00 (d, 2H), 7.60 (t, 1H), 7.54 (m, 3H), 7.39 (s, 1H), 6.88 (d, 1H), 4.33 (t, 2H), 3.85 (t, 2H), 3.63 (m, 2H), 3.48 (m, 2H), 3.25 (s, 3H): MS (+ve ESI): 460 (M+H)$^+$.

EXAMPLE 7

Preparation of Compound 7 in Table 1

2-(N-Benzoyl) 2,5-diaminopyrimidine (32 mg, 0.15 mmol) was added to a solution of N-acetyl-4-chloro-6-aminoquinoline (33 mg, 0.15 mmol) in isopropanol (2.0 ml) and the reaction heated at 82° C. for 3 hours before the reaction was allowed to cool to ambient temperature. Hydrochloric acid (0.15 ml of a 1.0 N solution in diethyl ether, 0.15 mmol) was added and the reaction heated at 82° C. for a further 3 hours before being allowed to cool to ambient temperature. Diethyl ether (7.5 ml) was added and the solid which precipitated was collected by suction. Purification by preparative reverse-phase hplc yielded the title compound (9.9 mg, 15% yield) as a white solid:

MS (+ve ESI): 399 (M+H)$^+$.

EXAMPLE 8

Preparation of Compound 8 in Table 1

An analogous reaction to that described in example 7, but starting with 4,5-dichloroquinoline (30 mg, 0.15 mmol), yielded the title compound (37.8 mg, 61% yield) as a white solid:

$^1$H-NMR (DMSO d$_6$): 11.24 (s, 1H), 8.54 (d, 1H, J=8 Hz), 8.08 (d, 1H, J=8 Hz), 7.87–7.99 (m, 4H), 7.50–7.64 (m, 3H), 6.94 (d, 1H, J=8 Hz): MS (+ve ESI): 376 (M+H)$^+$

EXAMPLE 9

Preparation of Compound 9 in Table 1

An analogous reaction to that described in example 7, but starting with 4-chloro-5-cyanoquinoline (29 mg, 0.15 mmol), yielded the title compound (26.7 mg, 44% yield) as a white solid:

$^1$H-NMR (DMSO d$_6$): 11.24 (s, 1H), 9.34 (s, 1H), 8.90 (s, 2H), 8.68 (d, 1H, J=8 HZ), 8.34 (d, 1H, J=8 Hz), 8.17 (d, 1H, J=8 Hz), 7.99 (d, 2H, J=8 Hz), 7.46–7.65 (m, 3H), 7.08 (d, 1H, J=8 Hz): MS (+ve ESI): 367 (M+H)$^+$ MS (–ve ESI): 365 (M–H)$^-$

EXAMPLE 10
Preparation of Compound 10 in Table 1

An analogous reaction to that described in example 7, but starting with 4-chloro-5,7-dimethylquinoline (29 mg, 0.15 mmol), yielded the title compound (5.6 mg, 9% yield) as a white solid:

$^1$H-NMR (DMSO d$_6$): 10.44 (bs, 1H), 8.48 (s, 2H), 8.00–8.04 (m, 3H), 7.33–7.62 (m, 6H), 7.06 (s, 1H), 2.93 (s, 3H), 2.44 (s, 3H): MS (+ve ESI): 370 (M+H)$^+$ MS (−ve ESI): 368 (M−H)$^−$.

EXAMPLE 11
Preparation of Compound 11 in Table 1

An analogous reaction to that described in example 7, but starting with 4,7-dichloroquinoline (30 mg, 0.15 mmol), yielded the title compound (28.3 mg, 46% yield) as a white solid:

$^1$H-NMR (DMSO d$_6$): 11.24 (s, 1H), 11.13 (s, 1H), 8.91 (s, 2H), 8.80 (d, 1H, J=8 Hz), 8.62 (d, 1H, J=8 Hz), 8.15 (s, 1H), 7.94–7.99 (m, 3H), 7.50–7.65 (m, 3H), 6.99 (d, 1H, J=8 Hz): MS (+ve ESI): 376 (M+H)$^+$.

EXAMPLE 12
Preparation of Compound 12 in Table 1

An analogous reaction to that described in example 7, but starting with 4-chloroquinoline (24 mg, 0.15 mmol), yielded the title compound (9.9 mg, 17% yield) as a white solid $^1$H-NMR (DMSO d$_6$): 11.02 (s, 1H), 8.79 (s, 2H), 8.48 (d, 1H, J=6 Hz), 8.39 (d, 1H, J=8 Hz), 7.98 (d, 2H, J=8 Hz), 7.91 (d, 1H, J=8 Hz), 7.72–7.78 (m, 1H), 7.48–7.63 (m, 4H), 6.87 (d, 1H, J=6 Hz): MS (+ve ESI): 342 (M+H)$^+$.

EXAMPLE 13
Preparation of Compound 13 in Table 1

An analogous reaction to that described in example 7, but starting with 4-chloro-7-(trifluoromethyl)quinoline (35 mg, 0.15 mmol), yielded the title compound (27.9 mg, 42% yield) as a white solid:

$^1$H-NMR (DMSO d$_6$): 11.25 (s, 1H), 9.00 (d, 1H, J=8 Hz), 8.92 (s, 2H), 8.74 (d, 1H, J=8 Hz), 8.45 (s, 1H), 8.20 (d, 1H, J=8 Hz), 7.99 (d, 2H, J=8 Hz), 7.50–7.64 (m, 4H), 7.10 (d, 1H, J=8 Hz): MS (+ve ESI): 410 (M+H)$^+$ MS (−ve ESI): 408 (M−H)$^−$.

EXAMPLE 14
Preparation of Compound 14 in Table 1

An analogous reaction to that described in example 7, but starting with 4-chloro-6-(trifluoromethyl)quinoline (35 mg, 0.15 mmol), yielded the title compound (7.5 mg, 11% yield) as a white solid:

MS (+ve ESI): 410 (M+H)$^−$.

Biological Data

The compounds of the invention inhibit the serine/threonine kinase activity of the aurora2 kinase and thus inhibit the cell cycle and cell proliferation. These properties may be assessed, for example, using one or more of the procedures set out below:

(a) In Vitro Aurora2 Kinase Inhibition Test

This assay determines the ability of a test compound to inhibit serine/threonine kinase activity. DNA encoding aurora2 may be obtained by total gene synthesis or by cloning. This DNA may then be expressed in a suitable expression system to obtain polypeptide with serine/threonine kinase activity. In the case of aurora2, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora2 coding sequence. This allowed the insertion of the aurora2 gene in frame with the 6 histidine residues, spacer region and rTEV protease cleavage site encoded by the pFastBac HTc vector. The 3' PCR primer replaced the aurora2 stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged aurora2 protein. Details of the methods for the assembly of recombinant DNA molecules can be found in standard texts, for example Sambrook et al. 1989, Molecular Cloning—A Laboratory Manual, 2$^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora2 gene was transformed into *E. coli* DH10Bac cells containing the baculovirus genome (bacmid DNA) and via a transposition event in the cells, a region of the pFastBac vector containing gentamycin resistance gene and the aurora2 gene including the baculovirus polyhedrin promoter was transposed directly into the bacmid DNA. By selection on gentamycin, kanamycin, tetracycline and X-gal, resultant white colonies should contain recombinant bacmid DNA encoding aurora2. Bacmid DNA was extracted from a small scale culture of several BH10Bac white colonies and transfected into Spodoptera frugiperda Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing 1×10$^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant aurora2 protein.

For the large scale expression of aurora2 kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached 1.2×10$^6$ cells ml$^{-1}$ they were infected with plaque-pure aurora2 recombinant virus at a multiplicity of infection of 1 and harvested 48 hours later. All subsequent purification steps were performed at 4° C. Frozen insect cell pellets containing a total of 2.0×10$^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 μg/ml aprotinin, 1 μg/ml pepstatin, 1 μg/ml leupeptin), using 1.0 ml per 3×10$^7$ cells. Lysis was achieved using a dounce homogeniser, following which the lysate was centrifuged at 41,000 g for 35 minutes. Aspirated supernatant was pumped onto a 5 mm diameter chromatography column containing 500 μl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora2 protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora2 kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora2 enzyme was titrated in the assay by dilution with enzyme diluent (25mM Tris-HCl pH7.5, 12.5 mM KCl, 0.6 mM DTT). For a typical batch, stock enzyme is diluted 1 in 666 with enzyme diluent & 20 $\mu$l of dilute enzyme is used for each assay well. Test compounds (at 10 mM in dimethylsulphoxide (DMSO)) were diluted with water & 10 $\mu$l of diluted compound was transferred to wells in the assay plates. "Total" & "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 78.4mM KCl, 2.5mM NaF, 0.6 mM dithiothreitol, 6.25 mM $MnCl_2$, 6.25 mM ATP, 7.5 $\mu$M peptide substrate [biotin-LRRWSLGLRRWSLGLRRWSLGLRRWSLG]) containing 0.2 $\mu$Ci [$\gamma^{33}$P]ATP (Amersham Pharmacia, specific activity $\geq$2500 Ci/mmol) was then added to all test wells to start the reaction. The plates were incubated at room temperature for 60 minutes. To stop the reaction 100 $\mu$l 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity.

For example, in this test, compounds 1, 2 and 4 in Table 1 gave 50% inhibition of enzyme activity at a concentration of 0.0521 $\mu$M, 0.059211 $\mu$M and 0.0785 $\mu$M respectively.

(b) In Vitro Cell Proliferation Assays

These and other assays can be used to determine the ability of a test compound to inhibit the growth of adherent mammalian cell lines, for example the human tumour cell line MCF7.

Assay 1

MCF-7 (ATCC HTB-22) or other adherent cells were typically seeded at 1×10$^3$ cells per well (excluding the peripheral wells) in DMEM (Sigma Aldrich) without phenol red, plus 10% foetal calf serum, 1% L-glutamine and 1% penicillin/streptomycin in 96 well tissue culture treated clear plates (Costar). The following day (day 1), the media was removed from a no treatment control plate and the plate stored at −80° C. The remaining plates were dosed with compound (diluted from 10 mM stock in DMSO using DMEM (without phenol red, 10% FCS, 1% L-glutamine, 1% penicillin/streptomycin). Untreated control wells were included on each plate. After 3 days in the presence/absence of compound (day 4) the media was removed and the plates stored at −80° C. Twenty four hours later the plates were thawed at room temperature and cell density determined using the CyQUANT cell proliferation assay kit (c-7026/c-7027 Molecular Probes Inc.) according to manufacturers directions. Briefly, 200 ml of a cell lysis/dye mixture (10 ml of 20× cell lysis buffer B, 190 ml of sterile water, 0.25 ml of CYQUANT GR dye) was added to each well and the plates incubated at room temperature for 5 minutes in the dark. The fluorescence of the wells was then measured using a fluorescence microplate reader (gain 70, 2 reads per well, 1 cycle with excitation 485 nm and emission 530 nm using a CytoFluor plate reader (PerSeptive Biosystems Inc.)). The values from day 1 and day 4 (compound treated) together with the values from the untreated cells were used to determine the dilution range of a test compound that gave 50% inhibition of cell proliferation. Compounds 1, 2 and 4 in Table 1 were effective in this test at concentrations of 0.36 mM, 0.456 mM and 0.185 mM respectively. These values could also be used to calculate the dilution range of a test compound at which the cell density dropped below the day 1 control value. This indicates the cytotoxicity of the compound.

Assay II

This assay determines the ability of at test compound to inhibit the incorporation of the thymidine analogue, 5'-bromo-2'-deoxy-uridine (BrdU) into cellular DNA. MCF-7 or other adherent cells were typically seeded at 0.8×10$^4$ cells per well in DMEM (Sigma Aldrich) without phenol red, plus 10% foetal calf serum, 1% L-glutamine and 1% penicillin/streptomycin (50 $\mu$l/well) in 96 well tissue culture treated 96 well plates (Costar) and allowed to adhere overnight. The following day the cells were dosed with compound (diluted from 10 mM stock in DMSO using DMEM (without phenol red, 10% FCS, 1% L-glutamine, 1% penicillin/streptomycin). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 $\mu$l of BrdU labelling reagent (diluted 1:100 in media—DMEM no phenol red, 10% FCS, 1% L-glutamine, 1% penicillin/streptomycin) was added to each well and the plate returned to a humidified (+5% $CO_2$) 37° C. incubator for 2 hours. After 2 hours the labelling reagent was removed by decanting and tapping the plate on a paper towel. FixDenat solution (50 $\mu$l per well) was added and the plates incubated at room temperature for 45 mins with shaking. The FixDenat solution was removed by decanting and tapping the inverted plate on a paper towel. The plate was then washed once with phosphate buffered saline (PBS) and 100 $\mu$l/well of Anti-BrdU-POD antibody solution (diluted 1:100 in antibody dilution buffer) added. The plate was then incubated at room temperature with shaking for 90 min. Unbound Anti-BrdU-POD antibody was removed by decanting and washing the plate 5 times with PBS before being blotted dry. TMB substrate solution was added (100 $\mu$l/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. For instance, compounds 1, 2 and 4 in Table 1 were effective in this test at 0.36 $\mu$M, 0.46 $\mu$M and 0.19 $\mu$M respectively.

(c) In Vitro Cell Cycle Analysis Assay

This assay determines the ability of a test compound to arrest cells in specific phases of the cell cycle. Many different mammalian cell lines could be used in this assay and MCF7 cells are included here as an example. MCF-7 cells were seeded at 3×10⁵ cells per T25 flask (Costar) in 5 ml DMEM (no phenol red 10% FCS, 1% L-glutamine 1% penicillin/streptomycin). Flasks were then incubated overnight in a humidified 37° C. incubator with 5% $CO_2$. The following day 1 ml of DMEM (no phenol red 10% FCS, 1% L-glutamine 1% penicillin/streptomycin) carrying the appropriate concentration of test compound solubilised in DMSO was added to the flask. A no compound control treatments was also included (0.5% DMSO). The cells were then incubated for a defined time (usually 24 hours) with compound. After this time the media was aspirated from the cells and they were washed with 5 ml of prewarmed (37° C.) sterile PBSA, then detached from the flask by brief incubation with trypsin and followed by resuspension in 10 ml of 1% Bovine Serum Albumin (BSA, Sigma-Aldrich Co.) in sterile PBSA. The samples were then centrifuged at 2200 rpm for 10 min. The supernatant was aspirated and the cell pellet was resuspended in 200 µl of 0.1% (w/v) Tris sodium citrate, 0.0564% (w/v) NaCl, 0.03% (v/v) Nonidet NP40, [pH 7.6]. Propridium Iodide (Sigma Aldrich Co.) was added to 40 µg/ml and RNAase A (Sigma Aldrich Co.) to 100 µg/ml. The cells were then incubated at 37 ° C. for 30 minutes. The samples were centrifuged at 2200 rpm for 10 min, the supernatant removed and the remaining pellet (nuclei) resuspended in 200 µl of sterile PBSA. Each sample was then syringed 10 times using 21 gauge needle. The samples were then transferred to LPS tubes and DNA content per cell analysed by Fluorescence activated cell sorting (FACS) using a FACScan flow cytometer (Becton Dickinson). Typically 25000 events were counted and recorded using CellQuest v1.1 software (Verity Software). Cell cycle distribution of the population was calculated using Modfit software (Verity Software) and expressed as percentage of cells in G0/G1, S and G2/M phases of the cell cycle.

Compounds of the invention showed activity in this assay.

What is claimed is:

1. A compound of formula (I)

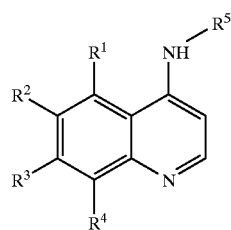

(I)

or a salt, in vivo hydrolysable ester or amide thereof;
where $R^5$ is a group of sub-formula (iii), (iv) or (v)

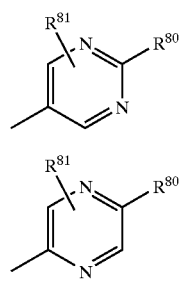

(iii)

(iv)

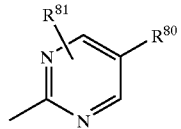

(v)

where $R^{80}$ is a substituent and $R^{81}$ is hydrogen or a substituent; where a substituent is independently selected from halo, $C_{1-4}$alkyl, optionally substituted $C_{1-6}$alkoxy (where suitable optional substituents are halo, perhaloalkyl, mercapto, thioalkyl, hydroxy, carboxy, alkoxy, heteroaryl, heteroaryloxy, cycloalkyl, cycloalkenyl, cycloalkynyl, alkenyloxy, alkynyloxy, alkoxyalkoxy, aryloxy (where the aryl group may be substituted by halo, nitro, or hydroxy), cyano, nitro, amino, mono- or di-alkyl amino, oximino or $S(O)_y R^{90}$ where y is 0 or an integer of 1–3 and $R^{90}$ is alkyl), $C_{1-4}$alkoxymethyl, di($C_{1-4}$alkoxy)methyl, $C_{1-4}$alkanoyl, trifluoromethyl, cyano, amino, $C_{2-5}$alkenyl, $C_{2-5}$alkynyl, a phenyl group, a benzyl group or a 5–6-membered heterocyclic group with 1–3 heteroatoms, selected independently from 0, S and N, which heterocyclic group may be aromatic or non-aromatic and may be saturated (linked via a ring carbon or nitrogen atom) or unsaturated (linked via a ring carbon atom), and which phenyl, benzyl or heterocyclic group may bear on one or more ring carbon atoms up to 5 substituents selected from hydroxy, halogeno, $C_{1-3}$alkyl, $C_{1-3}$alkoxy, $C_{1-3}$alkanoyloxy, trifluoromethyl, cyano, amino, nitro, $C_{2-4}$alkanoyl, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, $\underline{N}$—$C_{1-4}$alkylcarbamoyl, $\underline{N},\underline{N}$-di($C_{1-4}$alkyl)carbamoyl, aminosulphonyl, $\underline{N}$—$C_{1-4}$alkylaminosulphonyl, $\underline{N},\underline{N}$-di($C_{1-4}$alkyl)aminosulphonyl, $C_{1-4}$alkylsulphonylamino, and a saturated heterocyclic group selected from morpholino, thiomorpholino, pyrrolidinyl, piperazinyl, piperidinyl imidazolidinyl and pyrazolidinyl, which saturated heterocyclic group may bear 1 or 2 substituents selected from oxo, hydroxy, halogeno, $C_{1-3}$alkyl, $C_{1-3}$alkoxy, $C_{1-3}$alkanoyloxy, trifluoromethyl, cyano, amino, nitro and $C_{1-4}$alkoxycarbonyl; or a substituent is selected from carboxamido, carboxy and benzoyl; or a substituent is a group of sub-formula (II)

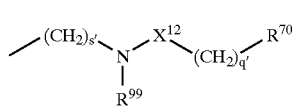

(II)

where q' is 0, 1, 2, 3 or 4;
s' is 0 or 1;
$X^{12}$ is C(O) or $S(O_2)$;
$R^{70}$ is hydrogen, hydroxy, $C_{1-6}$alkyl, $C_{1-6}$alkoxy, amino, $N$—$C_{1-6}$alkylamino, $N,N$-($C_{1-6}$alkyl)$_2$amino, hydroxy$C_{2-6}$alkoxy, $C_{1-6}$alkoxy$C_{2-6}$alkoxy, amino$C_{2-6}$alkoxy, $N$—$C_{1-6}$alkylamino$C_{2-6}$alkoxy, $N,N$-($C_{1-6}$alkyl)$_2$amino$C_{2-6}$alkoxy or $C_{3-7}$cycloalkyl,
or $R^{70}$ is of the Formula (III):

—K-J    (III)

wherein J is aryl, heteroaryl or heterocyclyl and K is a bond, oxy, imino, N—($C_{1-6}$alkyl)imino, oxy$C_{1-6}$alkylene, imino$C_{1-6}$alkylene, N—($C_{1-6}$alkyl)imino$C_{1-6}$alkylene, —NHC(O)—, —SO$_2$NH—, —NHSO$_2$— or —NHC(O)—$C_{1-6}$alkylene-, and any aryl, heteroaryl or heterocyclyl group in a $R^{70}$ group may be optionally substituted by one or more groups selected from hydroxy, halo, trifluoromethyl, cyano, mercapto, nitro, amino, carboxy, carbamoyl, formyl, sulphamoyl, $C_{1-6}$alkyl, $C_{2-6}$alkenyl, $C_{2-6}$alkynyl, $C_{1-6}$alkoxy, —O—($C_{1-3}$alkyl)—O—, $C_{1-6}$alkylS(O)$_n$— (wherein n is 0–2), N—$C_{1-6}$alkylamino, N,N-($C_{1-6}$alkyl)$_2$amino, $C_{1-6}$alkoxycarbonyl, N—$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N—$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N—($C_{1-6}$alkyl)amino, and suitably also oxo, or any aryl, heteroaryl or heterocyclyl group in a $R^{70}$ group may be optionally substituted with one or more groups of the Formula (IV):

$$—B^1—(CH_2)_p-A^1 \qquad (IV)$$

wherein $A^1$ is halo, hydroxy, $C_{1-6}$alkoxy, cyano, amino, N—$C_{1-6}$alkylamino, N,N-($C_{1-6}$alkyl)$_2$amino, carboxy, $C_{1-6}$alkoxycarbonyl, carbamoyl, N—$C_{1-6}$alkylcarbamoyl or N,N-($C_{1-6}$alkyl)$_2$carbamoyl, p is 1–6, and $B^1$ is a bond, oxy, imino, N—($C_{1-6}$alkyl)imino or —NHC(O)—, with the proviso that p is 2 or more unless $B^1$ is a bond or —NHC(O)—;

or any aryl, heteroaryl or heterocyclyl group in a $R^{70}$ group may be optionally substituted with one or more groups of the Formula (V):

$$-E^1-D^1 \qquad (V)$$

wherein $D^1$ is aryl, heteroaryl or heterocyclyl and $E^1$ is a bond, $C_{1-6}$alkylene, oxy$C_{1-6}$alkylene, oxy, imino, N—($C_{1-6}$alkyl)imino, imino$C_{1-6}$alkylene, N—($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N—($C_{1-6}$alkyl)-imino$C_{1-6}$alkylene, —NHC(O)—, —NHSO$_2$—, —SO$_2$NH— or —NHC(O)—$C_{1-6}$alkylene-, and any aryl, heteroaryl or heterocyclyl group in a substituent may be optionally substituted with one or more groups selected from hydroxy, halo, $C_{1-6}$alkyl, $C_{1-6}$alkoxy, carboxy, $C_{1-6}$alkoxycarbonyl, carbamoyl, N—$C_{1-6}$alkylcarbamoyl, N—($C_{1-6}$alkyl)$_2$carbamoyl, $C_{2-6}$alkanoyl, amino, N—$C_{1-6}$alkylamino and N,N-($C_{1-6}$alkyl)$_2$amino, and any $C_{3-7}$cycloalkyl or heterocyclyl group in a $R^{70}$ group may be optionally substituted with one or two oxo or thioxo substituents, and any of the $R^{70}$ groups defined hereinbefore which comprises a CH$_2$ group which is attached to 2 carbon atoms or a CH$_3$ group which is attached to a carbon atom may optionally bear on each said CH$_2$ or CH$_3$ group a substituent selected from hydroxy, amino, $C_{1-6}$alkoxy, N—$C_{1-6}$alkylamino, N,N-($C_{1-6}$alkyl)$_2$amino and heterocyclyl;

and $R^{99}$ is hydrogen or a group C(O)$R^{70}$ where $R^{70}$ is as defined above; or $R^{70}$ may be cycloalkenyl or cycloalkynyl, alkenyl optionally substituted by aryl or alkyl substituted by cycloalkenyl;

or a substituent is a group —$X^{10}$(CH$_2$)$_p$—$X^{11}R^{100}$ or —$X^{13}R^{100}$ where p' is 1–3, $X^{10}$ and $X^{11}$ are independently selected from a bond, —O—, —S— or NR$^{101}$— where $R^{101}$ is hydrogen or a $C_{1-3}$alkyl, provided that one of $X^{10}$ or $X^{11}$ is a bond; $X^{13}$ is —O—, —S— or NR$^{102}$—where $R^{102}$ is hydrogen or a $C_{1-4}$alkyl and $R^{100}$ is $R^{70}$;

or a substituent is a group of formula (VI)

where $R^{71}$ and $R^{72}$ are independently selected from hydrogen or $C_{1-4}$alkyl, or $R^{71}$ and $R^{72}$ together form a bond, and $R^{73}$ is a group OR$^{74}$, NR$^{75}R^{76}$ where $R^{74}$ is $C_{1-4}$alkyl and one of $R^{75}$ or $R^{76}$ is hydrogen and the other is $C_{1-6}$alkyl optionally substituted with trifluoromethyl, $C_{1-3}$ alkoxy, cyano, thio$C_{1-4}$alkyl, or indane or furan optionally substituted with $C_{1-4}$ alkyl, or one of $R^{75}$ or $R^{76}$ is hydrogen and the other is pyridine, or a phenyl group optionally substituted with one or more groups selected from halo, nitro, alkyl or alkoxy; and $R^{75}$ and $R^{76}$ may additionally form together with the nitrogen atom to which they are attached, an aromatic or non-aromatic heterocyclic ring which may contain further heteroatoms;

or a substituent is a group of sub-formula (VII)

where p" is 0 or 1 and $R^{83}$ and $R^{84}$ are $C_{1-4}$alkyl substituted by cycloalkyl; $C_{1-6}$alkylthio; $C_{1-6}$alkylthio; or a group —(CH$_2$)$_q R^{70}$ where q and $R^{70}$ are as defined above in relation to formula (II) or one of $R^{83}$ or $R^{84}$ is hydrogen, or methyl, ethyl or propyl optionally substituted with hydroxy or $R^{83}$ or $R^{84}$ is optionally substituted aryl group selected from phenyl optionally substituted with one or more groups selected from $C_{1-6}$alkyl or halo, hydroxy, alkoxy, trifluoromethyl, nitro, cyano, trifluromethoxy, CONH$_2$, C(O)CH$_3$, amino, or dimethylamine or $R^{83}$ or $R^{84}$ is an optionally substituted alkyl group selected from $C_{1-6}$alkyl group, optionally substituted with one or more cyano, hydroxy, alkoxy, alkylthio, COOalkyl, or aryl optionally substituted with $C_{1-6}$ alkyl or halo, hydroxy, alkoxy, trifluoromethyl, nitro, cyano, trifluromethoxy, CONH$_2$, C(O)CH$_3$, amino, or dimethylamine, or N-methyl pyrrole; or $R^{83}$ and $R^{84}$ is cyclohexyl optionally substituted with hydroxy; or $R^{83}$ and $R^{84}$ is prop-2-enyl; or $R^{83}$ or $R^{84}$ is optionally substituted heterocyclyl, or $R^{83}$ and $R^{84}$ together form a heterocyclic group, which may both be selected from piperadine, piperazine, morpholino, pyrrolidine or pyridine any of which may be optionally substituted with hydroxy, alkoxy, or alkyl which may itself be substituted with a hydroxy group;

and $R^1$, $R^2$, $R^3$, $R^4$ are independently selected from halogeno, cyano, nitro, $C_{1-3}$alkylsulphanyl, —N(OH)$R^7$— (wherein $R^7$ is hydrogen, or $C_{1-3}$alkyl), or $R^9X^1$—wherein at least one group $R^1$, $R^2$, $R^3$, $R^4$ is a group $R^9X^1$—(wherein $X^1$ represents a direct bond, —O—, —CH$_2$—, —OC(O)—, —C(O)—, —S—, —SO—, —SO$_2$—, —NR$^{10}$C(O)—, —C(O)NR$^{11}$—, —SO$_2$NR$^{12}$—, —NR$^{13}$SO$_2$— or —NR$^{14}$—(wherein $R^{10}$, $R^{11}$, $R^{12}$, $R^{13}$ and $R^{14}$ each independently represents hydrogen, hydroxyC$_{1-4}$alkyl C$_{1-3}$alkoxy or C$_{1-3}$alkoxyC$_{2-3}$alkyl)), and $R^9$ is selected from one of the following twenty-two groups:

1) hydrogen or C$_{1-5}$alkyl which may be unsubstituted or which may be substituted with one or more groups selected from hydroxy, oxiranyl, fluoro, chloro, bromo, amino, C$_{1-3}$alkyl and trifluoromethyl);

2) —R$^a$X$^2$C(O)R$^{15}$ (wherein X$^2$ represents —O— or —NR$^{16}$— (in which R$^{16}$ represents hydrogen, C$_{1-3}$alkyl or C$_{1-3}$alkoxyC$_{2-3}$alkyl) and R$^{15}$ represents C$_{1-3}$alkyl, —NR$^{17}$R$^{18}$ or —OR$^{19}$ (wherein R$^{17}$, R$^{18}$ and R$^{19}$ which may be the same or different each represents hydrogen, C$_{1-5}$alkyl, hydroxyC$_{1-5}$alkyl or C$_{1-3}$alkoxyC$_{2-3}$alkyl));

3) —R$^b$X$^3$R$^{20}$ (wherein X$^3$ represents —O—, C(O)—S—, —SO—, —SO$_2$—, —OC(O)—, —NR$^{21}$C(O)$_s$—, —C(O)NR$^{22}$—, —SO$_2$NR$^{23}$—, —NR$^{24}$SO$_2$— or —NR$^{25}$—(wherein R$^{21}$, R$^{22}$, R$^{23}$, R$^{24}$ and R$^{25}$ each independently represents hydrogen, C$_{1-3}$alkyl, hydroxy C$_{1-4}$alkyl or C$_{1-3}$alkoxyC$_{2-3}$alkyl and s is 1 or 2) and R$^{20}$ represents hydrogen, C$_{1-6}$alkyl, C$_{2-6}$alkenyl, cyclopropyl, cyclobutyl, cyclopentyl, cyclohexyl, phenyl or a 5–6-membered saturated heterocyclic group with 1–2 heteroatoms, selected independently from O, S and N, which C$_{1-6}$alkyl group may bear 1, 2 or 3 substituents selected from oxo, hydroxy, halogeno, cyclopropyl, amino, C$_{1-4}$alkylamino, C$_{1-4}$alkanoyldi-C$_{1-4}$alkylamino, C$_{1-4}$alkylthio, C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(R$^{b'}$)$_g$D (wherein f is 0 or 1, g is 0 or 1 and D is a cyclic group selected from C$_{3-6}$cycloalkyl group, an aryl group or a 5–6-membered saturated heterocyclic group with 1–2 heteroatoms, selected independently from O, S and N, which cyclic group may bear one or more substituents selected from halo or C$_{1-4}$alkyl));

4) —R$^c$X$^4$R$^{c'}$X$^5$R$^{26}$ (wherein X$^4$ and X$^5$ which may be the same or different are each —O—, C(O), —S—, —SO—, —SO$_2$—, —NR$^{27}$C(O)$_s$—, —C(O)$_x$NR$^{28}$—, —SO$_2$NR$^{29}$—, —NR$^{30}$SO$_2$— or —NR$^{31}$—(wherein R$^{27}$, R$^{28}$, R$^{29}$, R$^{30}$ and R$^{31}$ each independently represents hydrogen, C$_{1-3}$alkyl or C$_{1-3}$alkoxyC$_{2-3}$alkyl and s is 1 or 2) and R$^{26}$ represents hydrogen, C$_{1-3}$alkyl, hydroxyC$_{1-3}$alkyl or C$_{1-3}$alkoxyC$_{2-3}$alkyl);

5) R$^{32}$ wherein R$^{32}$ is a C$_{3-6}$ cycloalkyl or saturated heterocyclic ring (linked via carbon or nitrogen), with 1–2 heteroatoms, selected independently from O, S and N, which cycloalkyl or heterocyclic group may bear 1 or 2 substituents selected from oxo, hydroxy, halogeno, cyano, C$_{1-4}$alkyl, hydroxyC$_{1-4}$alkyl, cyanoC$_{1-4}$alkyl, cyclopropyl, C$_{1-4}$alkylsulphonylC$_{1-4}$alkyl, C$_{1-4}$alkoxycarbonyl, carboxamido, C$_{1-4}$aminoalkyl, C$_{1-4}$alkylamino, di(C$_{1-4}$alkyl)amino, C$_{1-4}$alkylaminoC$_{1-4}$alkyl, C$_{1-4}$alkanoyl, di(C$_{1-4}$alkyl) aminoC$_{1-4}$alkyl, C$_{1-4}$alkylaminoC$_{1-4}$alkoxy, di(C$_{1-4}$alkyl)aminoC$_{1-4}$alkoxy, nitro, amino, C$_{1-4}$alkoxy, C$_{1-4}$hydroxyalkoxy, carboxy, trifluoromethyl, —C(O)NR$^{38}$R$^{39}$, —NR$^{40}$C(O)R$^{41}$ (wherein R$^{38}$, R$^{39}$, R$^{40}$ and R$^{41}$, which may be the same or different, each represents hydrogen, C$_{1-4}$alkyl, hydroxyC$_{1-4}$alkyl or C$_{1-3}$alkoxyC$_{2-3}$alkyl) and a group —(—O—)$_f$(R$^{b'}$)$_g$D (wherein f is 0 or 1, g is 0 or 1 and D is a cyclic group selected from C$_{3-6}$cycloalkyl, aryl group or a 5–6-membered saturated or unsaturated heterocyclic group with 1–2 heteroatoms, selected independently from O, S and N, which cyclic group may bear one or more substituents selected from halo and C$_{1-4}$alkyl);

6) —R$^d$R$^{32}$ (wherein R$^{32}$ is as defined hereinbefore);
7) —R$^e$R$^{32}$ (wherein R$^{32}$ is as defined hereinbefore);
8) —R$^f$R$^{32}$ (wherein R$^{32}$ is as defined hereinbefore);
9) R$^{33}$ (wherein R$^{33}$ represents a pyridone group a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents selected from hydroxy, nitro, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, oxo, cyanoC$_{1-4}$alkyl, cyclopropyl, C$_{1-4}$alkylsulphonylC$_{1-4}$alkyl, C$_{1-4}$alkoxycarbonyl, di(C$_{1-4}$alkyl)amino, C$_{1-4}$alkylaminoC$_{1-4}$alkyl, C$_{1-4}$alkanoyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy, carboxy, carboxamido, trifluoromethyl, cyano, —C(O)NR$^{38}$R$^{39}$, —NR$^{40}$C(O)R$^{41}$ (wherein R$^{38}$, R$^{39}$, R$^{40}$ and R$^{41}$, which may be the same or different, each represents hydrogen, C$_{1-4}$alkyl, hydroxyC$_{1-4}$alkyl or C$_{1-3}$alkoxyC$_{2-3}$alkyl) and a group —(—O—)$_f$(C$_{1-4}$alkyl)$_g$D (wherein f is 0 or 1, g is 0 or 1 and D is a cyclic group selected from C$_{3-6}$cycloalkyl, aryl or 5–6-membered saturated or unsaturated heterocyclic group with 1–2 heteroatoms, selected independently from O, S and N, which cyclic group may bear one or more substituents selected from halo and C$_{1-4}$alkyl);

10) —R$^g$R$^{33}$ (wherein R$^{33}$ is as defined hereinbefore);
11) —R$^h$R$^{33}$ (wherein R$^{33}$ is as defined hereinbefore);
12) —R$^i$R$^{33}$ (wherein R$^{33}$ is as defined hereinbefore);
13) —R$^j$X$^6$R$^{33}$ (wherein X$^6$ represents —O—, —C(O)—, —S—, —SO—, —SO$_2$—, —OC(O)—, —NR$^{38}$C(O)—, —C(O)NR$^{39}$—, —SO$_2$NR$^{40}$—, —NR$^{41}$SO$_2$— or —NR$^{42}$—(wherein R$^{38}$, R$^{39}$, R$^{40}$, R$^{41}$ and R$^{42}$ each independently represents hydrogen, C$_{1-3}$alkyl, hydroxyC$_{1-3}$alkyl or C$_{1-3}$alkoxyC$_{2-3}$alkyl) and R$^{33}$ is as defined hereinbefore);

14) —R$^k$X$^7$R$^{33}$ (wherein X$^7$ represents —O—, C(O), —S—, —SO—, —SO$_2$—, —OC(O)—, —NR$^{43}$C(O)—, —C(O)NR$^{44}$—, —SO$_2$NR$^{45}$—, —NR$^{46}$SO$_2$— or —NR$^{47}$—(wherein R$^{43}$, R$^{44}$, R$^{45}$, R$^{46}$ and R$^{47}$ each independently represents hydrogen, C$_{1-3}$alkyl, hydroxyC$_{1-3}$alkyl or C$_{1-3}$alkoxyC$_{2-3}$alkyl) and R$^{33}$ is as defined hereinbefore);

15) —R$^m$X$^8$R$^{33}$ (wherein X$^8$ represents —O—, —C(O)—, —S—, —SO—, —SO$_2$—, —NR$^{48}$C(O)—, —C(O)NR$^{49}$—, —SO$_2$NR$^{50}$—, —NR$^{51}$SO$_2$— or —NR$^{52}$—(wherein R$^{48}$, R$^{49}$, R$^{50}$, R$^{51}$ and R$^{52}$ each independently represents hydrogen, C$_{1-3}$alkyl, hydroxyC$_{1-3}$alkyl or C$_{1-3}$alkoxyC$_{2-3}$alkyl) and R$^{33}$ is as defined hereinbefore);

16) —R$^n$X$^9$R$^{n'}$R$^{33}$ (wherein X$^9$ represents —O—, —C(O)—, —S—, —SO—, —SO$_2$—, —NR$^{53}$C(O)—,

37

—C(O)NR$^{54}$—, —SO$_2$NR$^{55}$—, NR$^{56}$SO$_2$— or —NR$^{57}$—(wherein R$^{53}$, R$^{54}$, R$^{55}$, R$^{56}$ and R$^{57}$ each independently represents hydrogen, C$_{1-3}$alkyl, hydroxyC$_{1-3}$alkyl or C$_{1-3}$alkoxyC$_{2-3}$alkyl) and R$^{33}$ is as defined hereinbefore);

17) —R$^p$X$^9$—R$^{p'}$R$^{32}$ (wherein X$^9$ and R$^{32}$ are as defined hereinbefore);

18) C$_{2-5}$alkenyl which may be unsubstituted or which may be substituted with one or more groups selected from hydroxy, fluoro, C$_{1-4}$alkylamino, N,N-di(C$_{1-4}$alkyl)amino, aminosulphonyl, N—C$_{1-4}$alkylaminosulphonyl, and N,N-di(C$_{1-4}$alkyl)aminosulphonyl;

19) C$_{2-5}$alkynyl which may be unsubstituted or which may be substituted with one or more groups selected from hydroxy, fluoro, C$_{1-4}$alkylamino, N,N-di(C$_{1-4}$alkyl)amino, aminosulphonyl, N—C$_{1-4}$alkylaminosulphonyl, and N,N-di(C$_{1-4}$alkyl)aminosulphonyl;

20) —R$^r$X$^9$R$^r$R$^{32}$ (wherein X$^9$ and R$^{32}$ are as defined hereinbefore);

21) —R$^u$X$^9$ R$^u$R$^{32}$ (wherein X$^9$ and R$^{32}$ are as defined hereinbefore); and 22) —R$^v$R$^{58}$(R$^{v'}$)$_q$(X$^9$)$_r$R$^{59}$(wherein X$^9$ is as defined hereinbefore, q is 0 or 1, r is 0 or 1, and R$^{58}$ is a C$_{1-3}$alkylene group or a cyclic group selected from cyclopropyl, cyclobutyl, cyclopentyl, cyclopentylene, cyclohexylene or a 5–6-membered saturated heterocyclic group with 1–2 heteroatoms, selected independently from O, S and N, which C$_{1-3}$alkylene group may bear 1, or 2 substituents selected from oxo, hydroxy, halogeno, and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ring D (wherein f is 0 or 1, g is 0 or 1 and ring D is a cyclic group selected from C$_{3-6}$cycloalkyl, aryl or 5–6-membered saturated or unsaturated heterocyclic group with 1–2 heteroatoms, selected independently from O, S and N, which cyclic group may bear one or more substituents selected from halo or C$_{1-4}$alkyl); and R$^{59}$ is hydrogen, C$_{1-3}$alkyl, or a cyclic group selected from cycloalkyl, cyclobutyl, cyclopentyl, cyclopentylene, cyclohexylene or a 5–6-membered saturated heterocyclic group with 1–2 heteroatoms, selected independently from O, S and N, which C$_{1-3}$alkyl group may bear 1, or 2 substituents selected from oxo, hydroxy, halogeno, and C$_{1-4}$alkoxy and which cyclic group may bear 1or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a cyclic group selected from C$_{3-6}$cycloalkyl, aryl or 5–6-membered saturated or unsaturated heterocyclic group with 1–2 heteroatoms, selected independently from O, S and N, which cyclic group may bear one or more substituents selected from halo or C$_{1-4}$alkyl);

38 and wherein R$^a$, R$^b$, R$^{b'}$, R$^c$, R$^{c'}$, R$^d$, R$^g$, R$^j$, R$^n$, R$^{n'}$, R$^p$, R$^{p'}$, R$^r$, R$^u$, R$^v$ and R$^{v'}$ are independently selected from C$_{1-8}$alkylene groups optionally substituted by one or more substituents selected from hydroxy, halogeno, amino, R$^e$R$^h$, R$^k$ and R$^t$ are independently selected from C$_{2-8}$alkenylene groups optionally substituted by one or more substituents selected from hydroxy, halogeno, amino, and R$^t$ may additionally be a bond; and R$^f$, R$^i$, R$^m$ and R$^u$ are independently selected from by C$_{2-8}$alkynylene groups optionally substituted by one or more substituents selected from hydroxy, halogeno, amino;

provided that at least one of R$^2$ or R$^3$ is other than hydrogen;

and wherein unless specifically stated, the terms heterocyclyl, heterocyclic group and heterocyclic ring include aromatic or non-aromatic rings containing from 4 to 20 ring atoms, at least one of which is a heteroatom selected from oxygen, sulphur or nitrogen.

2. A compound according to claim 1 where R$^1$ is hydrogen and R$^4$ is hydrogen, halo, C$_{1-4}$ alkyl or C$_{1-4}$alkoxy.

3. A compound according to claim 1 wherein at least one group R$^2$or R$^3$ comprises a chain of at least 3 optionally substituted carbon atoms or heteroatoms selected from oxygen, nitrogen or sulphur, wherein said chain is substituted by a polar group which assists solubility.

4. A compound of formula (VIII)

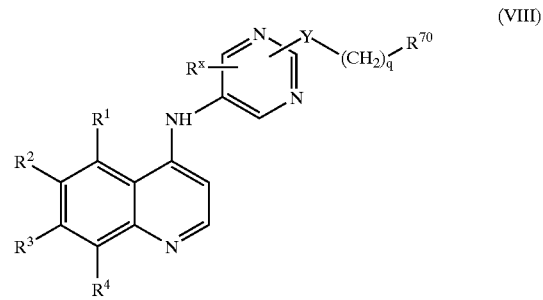

or a salt, in vivo hydrolysable ester or amide thereof;

where Y is a group —NR$^6$C(O)—, —C(O)NR$^6$—, —NR$^6$S(O)$_2$—, —NHR$^6$—, —NR$^6$CH=N—, —C(=NR$^6$)NR$^{6'}$—, —NR$^6$C(=NR$^{6'}$)NR$^{6''}$—, —C(O), —CH=CHC(O)NR$^6$—, —C≡CC(O)NR$^6$, —CH=CH—, —C≡C—, —S—, —S(O)—, —S(O)$_2$—, or —O—where R$^6$, R$^{6'}$ and R$^{6''}$ are independently selected from hydrogen or C$_{1-4}$alkyl, q is 0 or an integer of from 1 to 6;

R$^{70}$ is hydrogen, hydroxy, C$_{1-6}$alkyl, C$_{1-6}$alkoxy, amino, N—C$_{1-6}$alkylamino, N,N-(C$_{1-6}$alkyl)$_2$amino, hydroxyC$_{2-6}$alkoxy, C$_{1-6}$alkoxyC$_{2-6}$alkoxy, aminoC$_{2-6}$alkoxy N—C$_{1-6}$alkylaminoC$_{2-6}$alkoxy, N,N-(C$_{1-6}$alkyl)$_2$aminoC$_{2-6}$alkoxy or C$_{3-7}$cycloalkyl optionally substituted with one or two oxo or thioxo substituents, or R$^{70}$ is of the Formula (III):

—K-J  (III)

wherein J is an aryl or heterocyclyl group either of which is optionally substituted with one or more groups selected from hydroxy, halo, trifluoromethyl, cyano, mercapto, nitro, amino, carboxy, carbamoyl, formyl, sulphamoyl, C$_{1-6}$alkyl, C$_{2-6}$alkenyl, C$_{2-6}$alkynyl, $C_{1-6}$alkoxy, —O—($C_{1-3}$alkyl)—O—, $C_{1-6}$alkylS(O)$_n$—(wherein n is 0–2), N—$C_{1-6}$alkylamino, N,N-($C_{1-6}$alkyl)$_2$amino, $C_{1-6}$alkoxycarbonyl, N—$C_{1-6}$alkylcarbamoyl, N,N-($C_{1-6}$alkyl)$_2$carbamoyl, $C_{2-6}$alkanoyl, $C_{1-6}$alkanoyloxy, $C_{1-6}$alkanoylamino, N—$C_{1-6}$alkylsulphamoyl, N,N-($C_{1-6}$alkyl)$_2$sulphamoyl, $C_{1-6}$alkylsulphonylamino and $C_{1-6}$alkylsulphonyl-N—($C_{1-6}$alkyl)amino, or groups of the Formula (IV) or (V):

  (IV)

  (V)

wherein $A^1$ is halo, hydroxy, $C_{1-6}$alkoxy, cyano, amino, N—$C_{1-6}$alkylamino, N,N-($C_{1-6}$alkyl)$_2$amino, carboxy, $C_{1-6}$alkoxycarbonyl, carbamoyl, N—$C_{1-6}$ alkylcarbamoyl or N,N-($C_{1-6}$alkyl)$_2$carbamoyl, p is 1–6;

$B^1$ is a bond, oxy, imino, N—($C_{1-6}$alkyl)imino or —NHC(O)—, with the proviso that p is 2 or more unless $B^1$ is a bond or —NHC(O)—;

$D^1$ is aryl or heterocyclyl;

$E^1$ is a bond, $C_{1-6}$alkylene, oxy$C_{1-6}$alkylene, oxy, imino, N—($C_{1-6}$alkyl)imino, imino$C_{1-6}$alkylene, N—($C_{1-6}$alkyl)-imino$C_{1-6}$alkylene, $C_{1-6}$alkylene-oxy$C_{1-6}$alkylene, $C_{1-6}$alkylene-imino$C_{1-6}$alkylene, $C_{1-6}$alkylene-N—($C_{1-6}$alkyl)-imino$C_{1-6}$alkylene, —NHC(O)—, —NHSO$_2$—, —SO$_2$NH— or —NHC(O)—$C_{1-6}$alkylene-;

or, in the case of heterocyclyl groups J, these may be optionally substituted with one or two oxo or thioxo substituents;

and K is a bond, oxy, imino, N—($C_{1-6}$alkyl)imino, oxy$C_{1-6}$alkylene, imino$C_{1-6}$alkylene, N—($C_{1-6}$alkyl)imino$C_{1-6}$alkylene, —NHC(O)—, —SO$_2$NH—, —NHSO$_2$— or —NHC(O)—$C_{1-6}$alkylene-, $R^x$ is hydrogen, halo, $C_{1-4}$alkoxy, cyano, trifluoromethyl, or phenyl; and $R^1$, $R^2$, $R^3$, $R^4$ are independently selected from halo, cyano, nitro, trifluoromethyl, $C_{1-3}$alkyl, —NR$^7$R$^8$ (wherein $R^7$ and $R^8$, which may be the same or different, each represents hydrogen or $C_{1-3}$alkyl), or —X$^1$R$^9$ (wherein $X^1$ represents a direct bond, —O—, —CH$_2$—, —OCO—, carbonyl, —S—, —SO—, —SO$_2$—, —NR$^{10}$CO—, —CONR$^{11}$—, —SO$_2$NR$^{12}$—, —NR$^{13}$SO$_2$— or —NR$^{14}$— (wherein $R^{10}$, $R^{11}$, $R^{12}$, $R^{13}$ and $R^{14}$ each independently represents hydrogen, $C_{1-3}$alkyl or $C_{1-3}$alkoxy$C_{2-3}$alkyl), and $R^9$ is selected from one of the following eighteen groups:

1) hydrogen or $C_{1-5}$alkyl which may be unsubstituted or which may be substituted with one or more groups selected from hydroxy, fluoro or amino;

2) $C_{1-5}$alkylX$^2$COR$^{15}$ (wherein $X^2$ represents —O— or —NR$^{16}$—(in which $R^{15}$ represents hydrogen, $C_{1-3}$alkyl or $C_{1-3}$alkoxy$C_{2-3}$alkyl) and $R^{16}$ represents $C_{1-3}$alkyl, —NR$^{17}$R$^{18}$ or —OR$^{19}$ (wherein $R^{17}$, $R^{18}$, and $R^{19}$, which may be the same or different, each represent hydrogen, $C_{1-3}$alkyl or $C_{1-3}$alkoxy$C_{2-3}$alkyl));

3) $C_{1-5}$alkylX$^3$R$^{20}$ (wherein $X^3$ represents —O—, —S—, —SO—, —SO$_2$—, —OCO—, —NR$^{21}$CO—, —CONR$^{22}$—, —SO$_2$NR$^{23}$—, —NR$^{24}$SO$_2$— or —NR$^{25}$—(wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4) $C_{1-5}$alkylX$^4$C$_{1-5}$alkylX$^5$R$^{26}$ (wherein $X^4$ and $X^5$ which may be the same or different are each —O—, —S—, —SO—, —SO$_2$—, —NR$^{27}$CO—, —CONR$^{28}$—, —SO$_2$NR$^{29}$—, —NR$^{30}$SO$_2$— or —NR$^{31}$— (wherein $R^{27}$R$^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5) $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6) $C_{1-5}$alkylR$^{32}$ (wherein $R^{32}$ is as defined hereinbefore);

7) $C_{2-5}$alkenylR$^{32}$ (wherein $R^{32}$ is as defined hereinbefore);

8) $C_{2-5}$alkynylR$^{32}$ (wherein $R^{32}$ is as defined hereinbefore);

9) $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{34}$R$^{35}$ and —NR$^{36}$COR$^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl));

10) $C_{1-5}$alkylR$^{33}$ (wherein $R^{33}$ is as defined hereinbefore);

11) $C_{2-5}$alkenylR$^{33}$ (wherein $R^{33}$ is as defined hereinbefore);

12) $C_{2-5}$alkynylR$^{33}$ (wherein $R^{33}$ is as defined hereinbefore);

13) $C_{1-5}$alkylX$^6$R$^{33}$ (wherein $X^6$ represents —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{33}$ is as defined hereinbefore);

14) $C_{2-5}$alkenylX$^7$R$^{33}$ (wherein $X^7$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15) $C_{2-5}$alkynylX$^8$R$^{33}$ (wherein $X^8$ represents —O—, —S—, —SO—, —SO$_2$—, —NR$^{48}$CO—, —CONR$^{49}$—, —SO$_2$NR$^{50}$—, —NR$^{51}$SO$_2$— or —NR$^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy$C_{2-3}$alkyl) and $R^{33}$ is as defined hereinbefore);

16) $C_{1-3}$alkyl$X^9C_{1-3}$alkyl$R^{33}$ (wherein $X^9$ represents —O—, —S—, —SO—, —SO$_2$—, —NR$^{53}$CO—, —CONR$^{54}$—, —SO$_2$NR$^{55}$—, —NR$^{56}$SO$_2$— or —NR$^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17) $C_{1-3}$alkyl$X^9C_{1-3}$alkyl$R^{32}$ (wherein $X^9$ and $R^{28}$ are as defined hereinbefore);

and $R^1$ and $R^4$ may additionally be hydrogen.

5. A compound according to claim 4 where Y is a group —NR$^6$C(O)— or —C(O)NR$^6$— where $R^6$ is defined in claim 4.

6. A compound according to claim 1, wherein $R^{80}$ is a group of sub-formula (II) and $R^{81}$ is hydrogen or halo, $C_{1-4}$alkoxy, cyano, trifluoromethyl, or phenyl.

7. A compound according to claim 1 or claim 4, wherein $R^9$ is selected from one of the following groups:

1') hydrogen or $C_{1-5}$alkyl which may be unsubstituted or which may be substituted with one or more groups selected from hydroxy, fluoro or amino, 2') $C_{1-5}$alkyl$X^2$C(O)$R^{15}$ (wherein $X^2$ represents —O— or —NR$^{16}$— (in which $R^{15}$ represents hydrogen, $C_{1-3}$alkyl or $C_{1-3}$alkoxy$C_{2-3}$alkyl) and $R^5$ represents $C_{1-3}$alkyl, —NR$^{17}$R$^{18}$ or —OR$^{19}$ (wherein $R^{17}$, $R^{18}$ and $R^{19}$ which may be the same or different each represents hydrogen, $C_{1-3}$alkyl or $C_{1-3}$alkoxy$C_{2-3}$alkyl));

3') $C_{1-5}$alkyl$X^3R^{20}$ (wherein $X^3$ represents —O—, —S—, —SO—, —SO$_2$—, —OCO—, —NR$^{21}$CO—, —CONR$^{22}$—, —SO$_2$NR$^{23}$—, —NR$^{24}$SO$_2$— or —NR$^{25}$— (wherein $R^{21}$, $R^{22}$, $R^{23}$, $R^{24}$ and $R^{25}$ each independently represents hydrogen, $C_{1-3}$alkyl or $C_{1-3}$alkoxy$C_{2-3}$alkyl) and $R^{20}$ represents hydrogen, $C_{1-3}$alkyl, cyclopentyl, cyclohexyl or a 5–6-membered saturated heterocyclic group with 1–2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);

4') $C_{1-5}$alkyl$X^4C_{1-5}$alkyl$X^5R^{26}$ (wherein $X^4$ and $X^5$ which may be the same or different are each —O—, —S—, —SO—, —SO$_2$—, —NR$^{27}$CO—, —CONR$^{28}$—, —SO$_2$NR$^{29}$—, —NR$^{30}$SO$_2$— or —NR$^{31}$— (wherein $R^{27}$, $R^{28}$, $R^{29}$, $R^{30}$ and $R^{31}$ each independently represents hydrogen, $C_{1-3}$alkyl or $C_{1-3}$alkoxy$C_{2-3}$alkyl) and $R^{26}$ represents hydrogen or $C_{1-3}$alkyl);

5') $R^{32}$ (wherein $R^{32}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);

6') $C_{1-5}$alkyl$R^{32}$ (wherein $R^{32}$ is as defined in (5') above);

7') $C_{2-5}$alkenyl$R^{32}$ (wherein $R^{32}$ is as defined in (5') above);

8') $C_{2-5}$alkynyl$R^{32}$ (wherein $R^{32}$ is as defined in (5') above);

9') $R^{33}$ (wherein $R^{33}$ represents a pyridone group, a phenyl group or a 5–6-membered aromatic heterocyclic group (linked via carbon or nitrogen) with 1–3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —CONR$^{34}$R$^{35}$ and —NR$^{36}$COR$^{37}$ (wherein $R^{34}$, $R^{35}$, $R^{36}$ and $R^{37}$, which may be the same or different, each represents hydrogen, $C_{1-4}$alkyl or $C_{1-3}$alkoxy$C_{2-3}$alkyl));

10') $C_{1-5}$alkyl$R^{33}$ (wherein $R^{33}$ is as defined in (9') above);

11') $C_{2-5}$alkenyl$R^{33}$ (wherein $R^{33}$ is as defined in (9') above);

12') $C_{2-5}$alkynyl$R^{33}$ (wherein $R^{33}$ is as defined in (9') above);

13') $C_{1-5}$alkyl$X^6R^{33}$ (wherein $X^6$ represents —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{33}$ is as defined hereinbefore);

14') $C_{2-5}$alkenyl$X^7R^{33}$ (wherein $X^7$ represents —O—, —S—, —SO—, —SO$_2$—, —NR$^{43}$CO—, —CONR$^{44}$—, —SO$_2$NR$^{45}$—, —NR$^{46}$SO$_2$— or —NR$^{47}$— (wherein $R^{43}$, $R^{44}$, $R^{45}$, $R^{46}$ and $R^{47}$ each independently represents hydrogen, $C_{1-3}$alkyl or $C_{1-3}$alkoxy$C_{2-3}$alkyl) and $R^{33}$ is as defined hereinbefore);

15') $C_{2-5}$alkynyl$X^8R^{33}$ (wherein $X^8$ represents —O—, —S—, —SO—, —SO$_2$—, —NR$^{48}$CO—, —C(O)NR$^{49}$—, —SO$_2$NR$^{50}$—, —NR$^{51}$SO$_2$— or —NR$^{52}$— (wherein $R^{48}$, $R^{49}$, $R^{50}$, $R^{51}$ and $R^{52}$ each independently represents hydrogen, $C_{1-3}$alkyl or $C_{1-3}$alkoxy $C_{2-3}$alkyl) and $R^{33}$ is as defined hereinbefore);

16') $C_{1-3}$alkyl$X^9C_{1-3}$alkyl$R^{33}$ (wherein $X^9$ represents —O—, —S—, —SO—, —SO$_2$—, —NR$^{53}$CO—, —C(O)NR$^{54}$—, —SO$_2$NR$^{55}$—, —NR$^{56}$SO$_2$— or —NR$^{57}$— (wherein $R^{53}$, $R^{54}$, $R^{55}$, $R^{56}$ and $R^{57}$ each independently represents hydrogen, $C_{1-3}$alkyl or $C_{1-3}$alkoxy$C_{2-3}$alkyl) and $R^{33}$ is as defined hereinbefore); and 17') $C_{1-3}$alkyl$X^9C_{1-3}$alkyl$R^{32}$ (wherein $X^9$ and $R^{32}$ are as defined in (5') above); provided that least one of $R^2$ or $R^3$ is other than hydrogen.

8. A compound according to claim 1 or claim 4, wherein $R^9$ is selected from the groups (1), (3), (6) or (10).

9. A compound according to claim 4 of formula (IX)

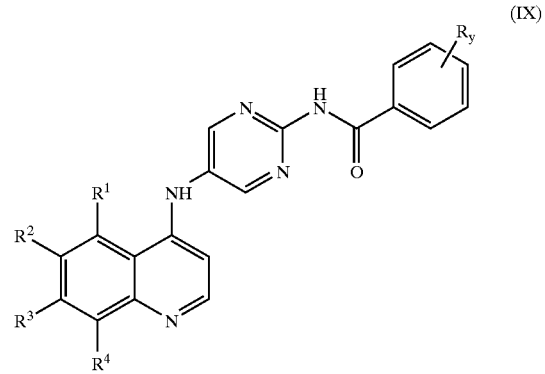

(IX)

where $R^1$, $R^2$, $R^3$ and $R^4$ are as defined in claim 4 and $R^y$ is hydrogeno or halogeno.

10. A process for preparing a compound of formula (VIII), which process comprises reacting a compound of formula (X)

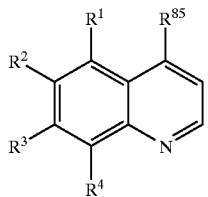

(X)

where $R^1$, $R^2$, $R^3$, and $R^4$ are as defined in claim 4 and $R^{85}$ is a leaving group, with a compound of formula (XI)

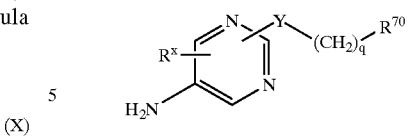

(XI)

where $R^x$, Y, q and $R^{70}$ are as defined in claim 4.

11. A method for inhibiting aurora 2 kinase in a warm blooded animal, which comprises administering to said animal an effective amount of a compound of formula (I), or a pharmaceutically acceptable salt, or an in vivo hydrolysable ester thereof.

12. A pharmaceutical composition comprising a compound according to claim 1 or salt, in vivo hydrolysable ester or amide thereof, in combination with a pharmaceutically acceptable carrier.

* * * * *